United States Patent
Nishino et al.

[11] Patent Number: 5,814,634
[45] Date of Patent: Sep. 29, 1998

[54] ALKYLENEDIAMINE DERIVATIVE ANTI-ULCER DRUG AND ANTIBACTERIAL DRUG

[75] Inventors: Chikao Nishino; Fumitaka Sato, both of Yokohama; Tomohiro Uetake, Tokyo; Hirotada Fukunishi, Yokohama; Nao Kojima, Tokyo, all of Japan

[73] Assignee: Shiseido Co. Ltd., Tokyo, Japan

[21] Appl. No.: 842,891

[22] Filed: Apr. 17, 1997

[30] Foreign Application Priority Data

| Apr. 18, 1996 | [JP] | Japan | 8-122195 |
| Sep. 30, 1996 | [JP] | Japan | 8-278871 |
| Jan. 6, 1997 | [JP] | Japan | 9-012056 |

[51] Int. Cl.$^6$ ............ A61K 31/535; C07D 265/30; C07D 211/32
[52] U.S. Cl. ............ 514/237.8; 514/331; 544/160; 544/169; 544/400; 546/233; 546/234
[58] Field of Search ............ 544/160, 169, 544/400; 546/233, 234; 514/237.8, 331

[56] References Cited

FOREIGN PATENT DOCUMENTS

| 1-168678 | of 0000 | Japan. |
| 2-207069 | of 0000 | Japan. |
| 40-19344 | of 0000 | Japan. |
| 5-239005 | of 0000 | Japan. |
| WO 95 04049 | 2/1995 | WIPO. |

Primary Examiner—John Kight
Assistant Examiner—Raymond Covington
Attorney, Agent, or Firm—Ronald R. Snider

[57] ABSTRACT

The invention provides a compound which has anti-ulcer effect and antibacterial activity against *Helicobacter pyroli*. This compound is an alkylenediamine derivative or salt which has a general formula of (1):

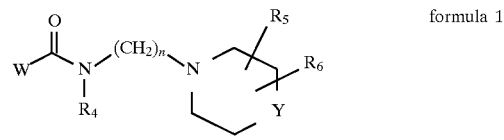

formula 1 wherein each of $R_4$, $R_5$, and $R_6$ is hydrogen or lower alkyl; n represents an integer of 1 to 6; Y is —$CH_2$—, —O—, or —N($R_7$)—, wherein $R_7$ is lower alkyl, aryl, carbamoyl lower alkyl, aralkyl, or a heterocyclic group having 5 to 9 carbon numbers; and, W is a group expressed by formulas 2 or 3:

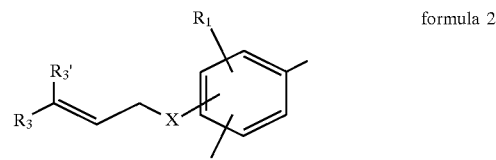

formula 2

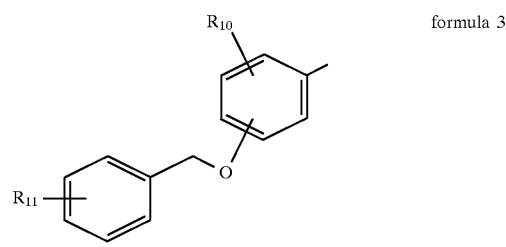

formula 3 wherein (1) in formula 2: each of $R_1$ and $R_2$ is hydrogen, lower alkoxy, alkenyloxy, or a halogen atom; each of $R_3$ and $R_3'$ is methyl, prenyl, or geranyl; when one of $R_3$ and $R_3'$ is prenyl or geranyl, the other must be a methyl group; and X is oxygen or sulfur; and (2) in formula 3, $R_{10}$ is a lower alkyl, and $R_{11}$ is a halogen atom.

26 Claims, 3 Drawing Sheets

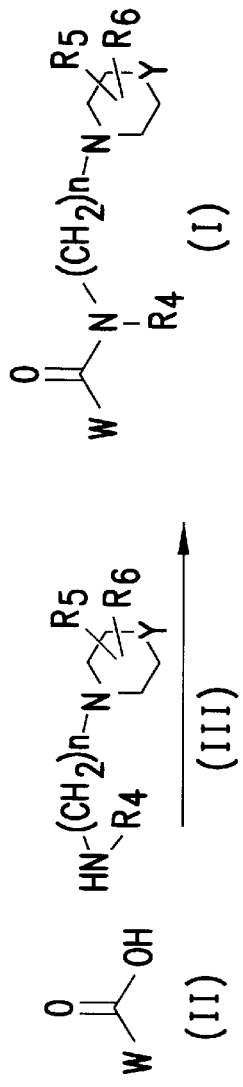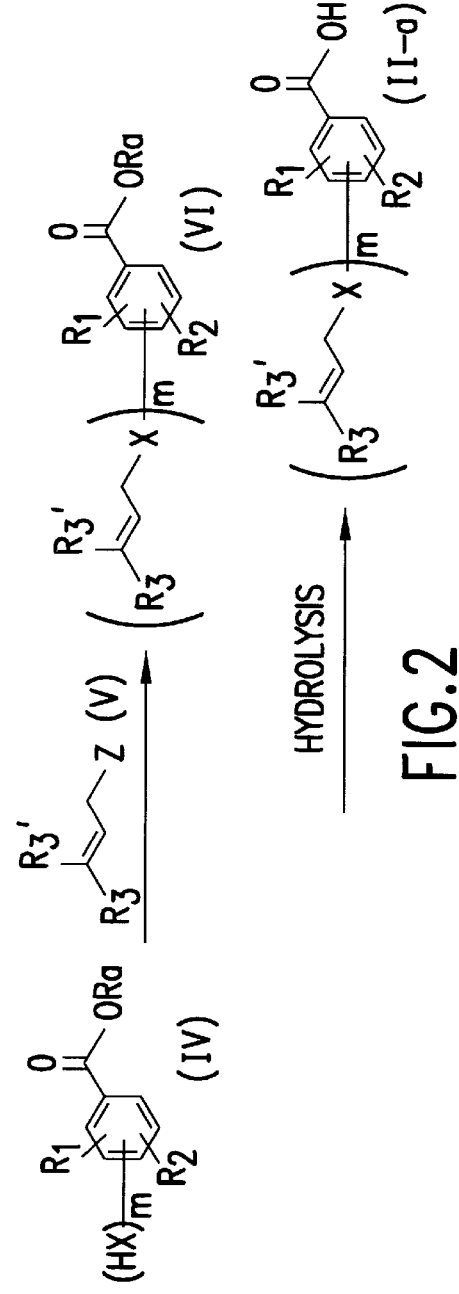

REACTION FORMULA C:

REACTION FORMULA D:

REACTION FORMULA E:
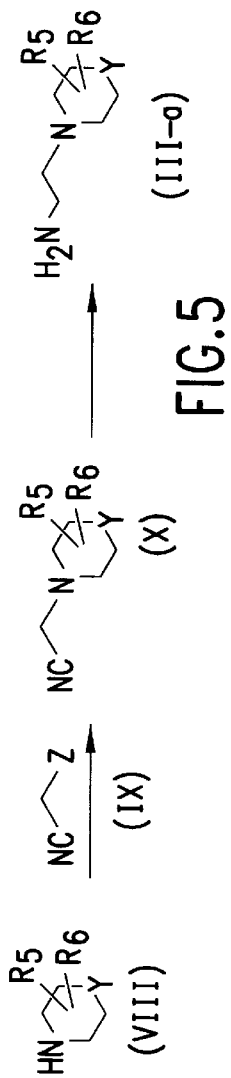
FIG.5
REACTION FORMULA F:
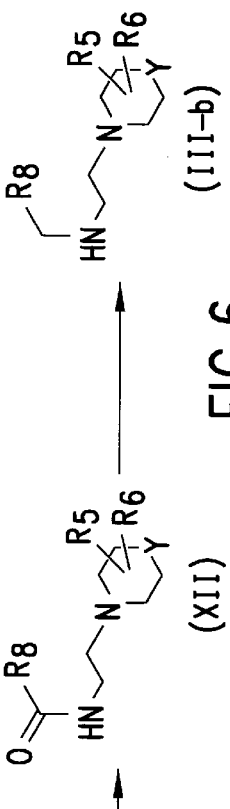
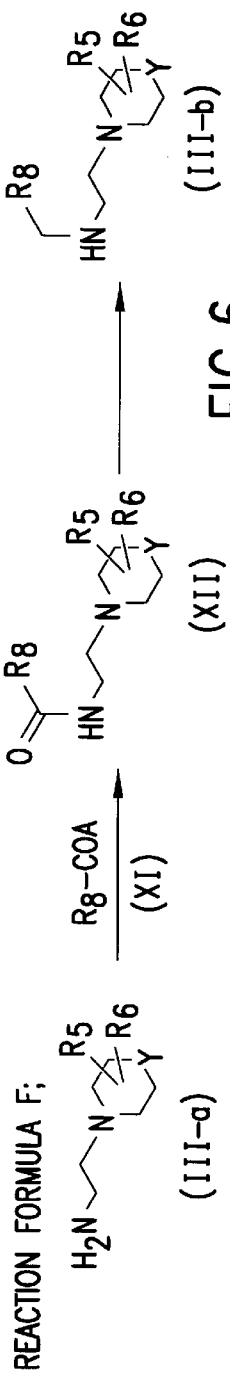
FIG.6
REACTION FORMULA G:
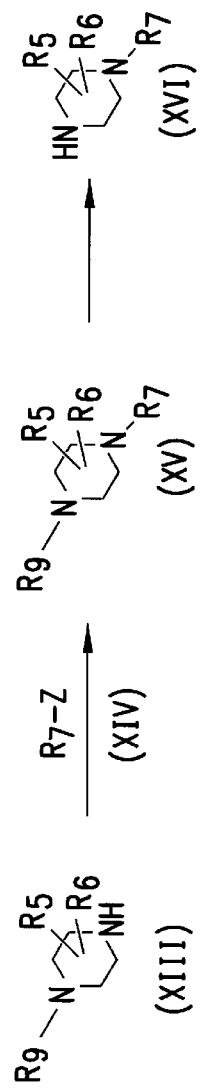
FIG.7

ALKYLENEDIAMINE DERIVATIVE ANTI-ULCER DRUG AND ANTIBACTERIAL DRUG

RELATED APPLICATIONS

This application claims the priority of Japanese Patent Application No. 8-122195 filed on Apr. 18, 1996, Japanese Patent Application No. 8-278871 filed on Sep. 30, 1996, Japanese Patent Application No. 9-12056 filed on Jan. 6, 1997, which are incorporated herein by references.

FIELD OF THE INVENTION

The present invention relates to an alkylenediamine derivative and, in particular, to an alkylenediamine derivative having an antibacterial activity against *Helicobacter pyroli* or an anti-ulcer effect.

BACKGROUND OF THE INVENTION

Various theories have been proposed with respect to a cause of ulcer in human. In particular, it has been elucidated that stress, taking of non-steroidal anti-inflammatory drugs for curing rheumatic diseases, and the like are closely related to ulcer formation, mainly due to relatively excess gastric acid secretion. Accordingly, it is important to suppress the acid secretion in order to prevent ulcer formation and to cure it.

On the other hand, it has been considered that *Helicobacter pyroli*, which is a rod normally existing in stomach, generates ammonia due to its strong urease activity, thereby inducing ulcer and persistence of itself. Since it persistently lives within mucus and mucosa, it becomes the greatest cause for recurrence of ulcer. Accordingly, it has been considered that the recurrence of ulcer can be prevented if this bacterium is sterilized.

Though various kinds of medicaments for curing ulcer have been conventionally developed, few medicaments have been known to have an effect for preventing stress ulcers from generating and an antibacterial activity against *Helicobacter pyroli*.

DISCLOSURE OF THE INVENTION

In view of the problems of the above-mentioned prior art, the object of the present invention is to provide a compound which is excellent in preventing ulcer from generating and to provide antibacterial drug against *Helicobacter pyroli* and anti-ulcer drug including such a compound as a main component.

As a result of the diligent studies conducted by the inventors, it has been found that a specific alkylenediamine derivative is effective against various kinds of ulcer due to its antibacterial property against *Helicobacter pyroli* or its acid secretion inhibition as a main action mechanism. Thus, the present invention has been accomplished.

Namely, an alkylenediamine derivative or a salt thereof in accordance with the present invention is expressed by the following formula 1:

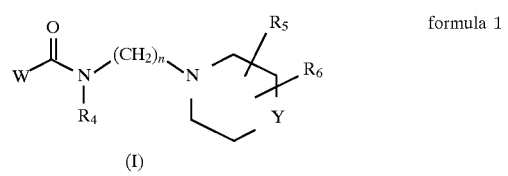

(I)

wherein W represents a group expressed by the following formula 2 or formula 3;

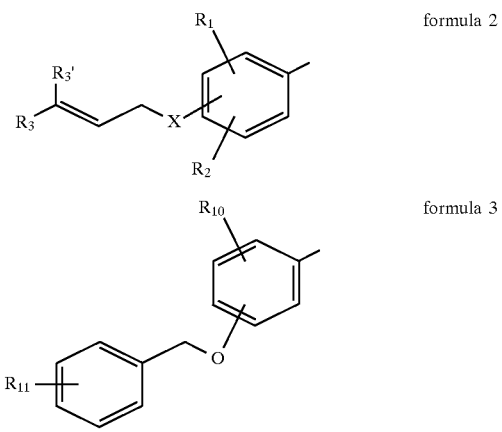

wherein each of $R_1$ and $R_2$ represents hydrogen atom, a lower alkoxy group, an alkenyloxy group, or a halogen atom;

each of $R_3$ and $R_3'$ represents methyl group, prenyl group, or geranyl group and when one of $R_3$ and $R_3'$ is prenyl group or geranyl group, another is methyl group;

X represents oxygen atom or sulfur atom;

$R_{10}$ represents a lower alkyl group; and $R_{11}$ represents a halogen atom; and wherein each of $R_4$, $R_5$, and $R_6$ represents hydrogen atom or a lower alkyl group;

Y represents a group expressed by $-CH_2-$, $-O-$, or $-N(R_7)-$, while $R_7$ represents a lower alkyl group, an aryl group, a carbamoyl lower alkyl group, an aralkyl group, or a heterocyclic group having 5 to 9 members; and n represents an integer of 1 to 6.

An anti-ulcer drug in accordance with the present invention comprises, as an effective ingredient, said alkylenediamine derivative or the pharmacologically acceptable salt thereof, together with a pharmaceutically acceptable carrier and/or adjuvant.

An antibacterial drug against *Helicobacter pyroli* in accordance with the present invention comprises, as an effective ingredient, said alkylenediamine derivative or the pharmacologically acceptable salt thereof, together with a pharmaceutically acceptable carrier and/or adjuvant A method for the treatment of peptic ulcers in man or mammals in accordance with the present invention comprises administering an effective amount of said alkylenediamine derivative or the pharmacologically acceptable salt thereof to a host.

A method for the inhibition of acid secretion in stomach of man or mammals in accordance with the present invention comprises administering an effective amount of said alkylenediamine derivative or the pharmacologically acceptable salt thereof to a host.

A method for the inhibition of growth of *Helicobacter pyroli* in stomach of man or mammals in accordance with the present invention comprises administering an effective amount of said alkylenediamine derivative or the pharmacologically acceptable salt thereof to a host.

A method for the prevention of peptic ulcers in man or mammals in accordance with the present invention comprises administering an effective amount of said alkylenediamine derivative or the pharmacologically acceptable salt thereof to a host.

BRIEF DESCRIPTION OF THE DRAWINGS

FIG. 1 shows an example of a step for manufacturing the alkylenediamine derivative in accordance with the present invention and FIGS. 2 to 7 show examples of steps for manufacturing material compounds for the alkylenediamine derivative in accordance with the present invention.

EXAMPLES

Figure 3:
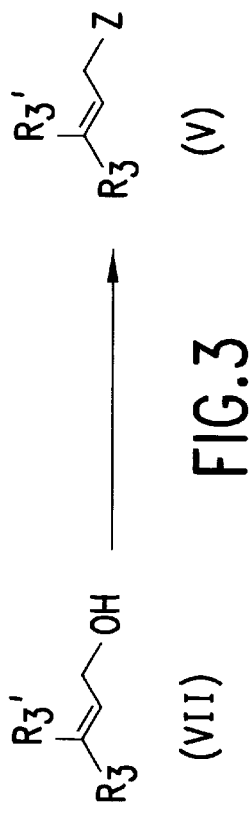
Figure 4:
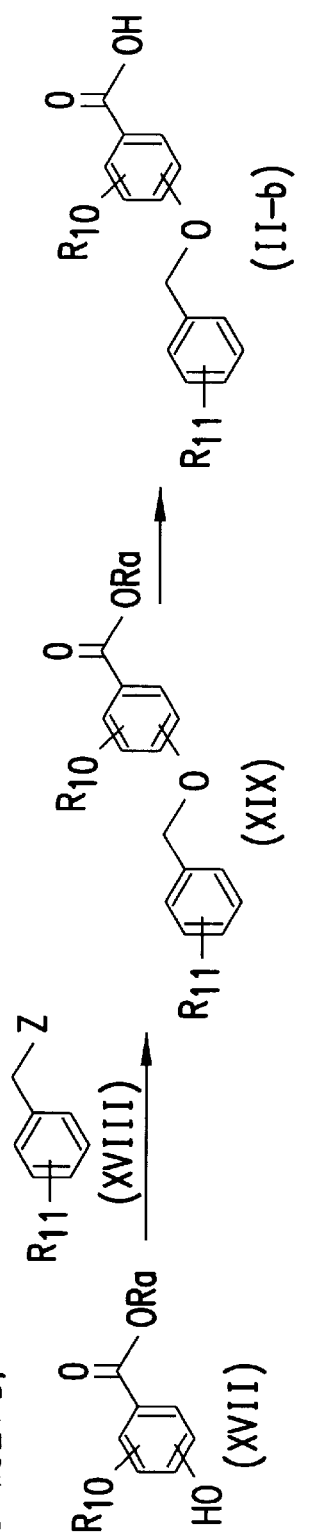

In the compound in accordance with the present invention, the lower alkoxy group found at $R_1$ and $R_2$ is a straight or branched alkoxy group having 1 to 6 carbon atoms. Examples thereof include methoxy, ethoxy, n-propyloxy, n-butyloxy, isopropyloxy, isobutyloxy, 1-methylpropyloxy, tert-butyloxy, n-pentyloxy, 1-ethylpropyloxy, isoamyloxy, and n-hexyloxy group. Preferably, they are methoxy groups.

The alkenyl group of "alkenyloxy group" found at $R_1$ and $R_2$ represents a straight or branched alkenyl group which has at least one double bond and has 2 to 20 carbon atoms. While the double bond has two kinds of configurations, namely, cis and trans, each double bond in alkenyl group may have either configurations. It is preferably a branched alkenyl group from the viewpoint of effect. Particularly, prenyl group, geranyl group, neryl group or farnesyl group is preferable.

In the present invention, each of $R_1$ and $R_2$, which may be identical to or different from each other, can be hydrogen atom, said lower alkoxy group, said alkenyloxy group, or a halogen atom.

The lower alkyl group found at $R_4$, $R_5$, $R_6$, $R_7$, and $R_{10}$ is a straight or branched alkyl group having 1 to 8 carbon atoms. Examples thereof include methyl, ethyl, n-propyl, n-butyl, isopropyl, isobutyl, 1-methylpropyl, tert-butyl, n-pentyl, 1-ethylpropyl, isoamyl, n-hexyl, and 2-ethylhexyl group. A preferable example of $R_4$ is ethyl group. A preferable example of $R_5$ and $R_6$ is methyl group. A preferable example of $R_7$ is ethyl or isobutyl group. A preferable example of $R_{10}$ is isobutyl group.

Each of $R_4$, $R_5$, and $R_6$, which may be identical to or different from each other, can be hydrogen atom said lower alkyl group.

$R_7$ can be the said lower alkyl group, an aryl group, a carbamoyl lower alkyl group, an aralkyl group, or an unsaturated heterocyclic group having 5 to 9 members.

Examples of the aryl group found at $R_7$ include phenyl group and naphtyl group. A preferable example thereof is phenyl group. Also, the aryl group can have a substituted group on its aromatic ring. Examples of such a substituted group include a lower alkoxy group. Here, the lower alkoxy group is defined as above and is preferably methoxy group.

The carbamoyl lower alkyl group found at $R_7$ represents a group in which a hydrogen atom of a lower alkyl group is substituted by a carbamoyl group—$CONH_2$. Here, the lower alkyl group is defined as above. A preferable example thereof is a straight lower alkyl group and, particularly, methyl group. Also, the hydrogen atom of the carbamoyl group can be substituted by a lower alkyl group. Such a lower alkyl group can be exemplified by the above-mentioned lower alkyl group and is preferably isopropyl group. Also, the nitrogen atom of the carbamoyl group can be a member of a saturated heterocyclic group to form it. A preferable example of such a heterocyclic group is pyrrolidino group.

Examples of the aralkyl group found at $R_7$ include benzyl group and phenethyl group. A preferable example thereof is benzyl group. Also, the aralkyl group can have a substituted group on its aromatic ring. Examples of such a substituted group include a halogen atom and a methylenedioxy group.

Preferably examples of such a substituted aralkyl group are fluorobenzyl group and 3,4-methylenedioxybenzyl group.

Examples of the unsaturated heterocyclic group having 5 to 9 members found at $R_7$ include a group contained nitrogen and/or oxygen atom. Preferable examples thereof are thiazolyl, benzothiazolyl, and pyrimidinyl group.

A preferable compound of the present invention may be expressed by the following formula 4:

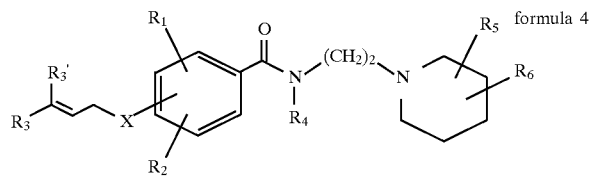

formula 4 wherein $R_1$, $R_2$, $R_3$, $R_3'$, $R_4$, $R_5$, $R_6$, and X are same as those in the above mentioned formula 1.

In formula 4, it is preferable that X is oxygen atom, while $R_4$, $R_5$, and $R_6$ are hydrogen atoms.

In formula 4, it is preferable that $R_1$ and $R_2$ are hydrogen atoms.

In formula 4, it is preferable that $R_1$ and/or $R_2$ is an alkenyloxy group expressed by the following formula 5;

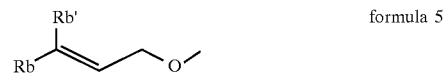

formula 5 wherein each of $R_b$ and $R_b'$ represents methyl group, prenyl group, or geranyl group and when one of $R_b$ and $R_b'$ is prenyl group or geranyl group, another is methyl group.

In formula 4, it is preferable that $R_1$ and/or $R_2$ is a lower alkoxy group.

A preferable compound of the present invention may be expressed by the following formula 6:

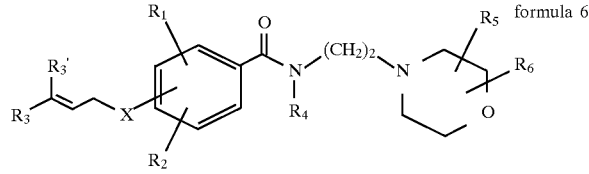

formula 6 wherein $R_1$, $R_2$, $R_3$, $R_3'$, $R_4$, $R_5$, $R_6$, and X are same as those in the above-mentioned formula 1.

In formula 6, it is preferable that X is oxygen atom, while $R_4$, $R_5$, and $R_6$ are hydrogen atoms.

In formula 6, it is preferable that $R_1$ and $R_2$ are hydrogen atoms.

In formula 6, it is preferable that $R_1$ and/or $R_2$ is an alkenyloxy group expressed by above-mentioned formula 5.

In formula 6, it is preferable that $R_1$ and/or $R_2$ is a lower alkoxy group.

A preferable compound of the present invention may be expressed by the following formula 7:

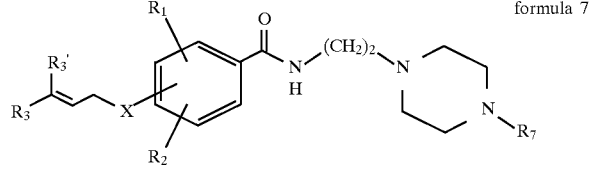

formula 7 wherein $R_1$, $R_2$, $R_3$, $R_3'$, $R_7$, and X are same as those in the above-mentioned formula 1.

In formula 7, it is preferable that X is oxygen atom, while $R_1$ and $R_2$ are hydrogen atoms.

A preferable compound of the present invention may be expressed by the following formula 8:

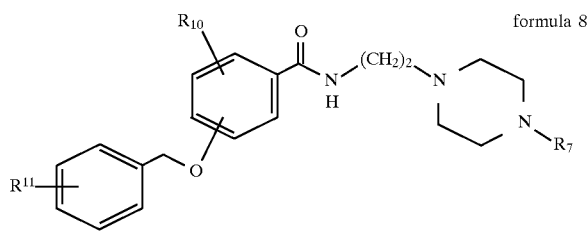

formula 8 wherein $R_7$ is a lower alkyl group; and $R_{10}$ and $R_{11}$ are same as those in the above-mentioned formula 3.

In formula 8, it is preferable that $R_7$ and $R_{10}$ are isobutyl groups.

In formula 8, it is preferable that $R_{11}$ is fluorine atom bonded to para-position.

The alkylenediamine derivatives and its pharmacologically acceptable salts in accordance with the present invention have anti-ulcer effect, acid secretion inhibition effect, and anti-bacterial effect against *Helicobacter pyroli* as well as a high safety. Accordingly, they are useful as medicaments for preventing and curing various kinds ulcer.

As similar compounds to the present invention, there have been known an alkylenediamine derivative having an analgic action and spasmolysis effect in stomach and bowel in Japanese Examined Patent Publication No. 40-19344, an alkylenediamine derivative having a gastric movement accelerating effect and an emesis effect in Japanese Unexamined Patent Publication No. 1-168678, an alkylenediamine derivative having an enterokinesis accelerating effect in Japanese Unexamined Patent Publication No. 2-207069, and an alkylenediamine derivative having a cerebrovascular damage ameliorating effect in Japanese Unexamined Patent Publication No. 5-239005. However, all of them do not relate to the pharmacological effect of the present invention. Also, the alkylenediamine derivative in accordance with the present invention is characterized in that W in the basic skeleton of formula 1 is a phenyl group having 1 to 3 alkenyloxy groups on its aromatic ring as shown in formula 2, or a phenyl group having both of a benzyloxy group and a lower alkyl group on its aromatic ring as shown in formula 3. Such an alkylenediamine derivative has not been known even from the viewpoint of structure. Accordingly, the alkylenediamine derivative of the present invention is a novel compound completely.

In the following, while the general method for manufacturing the compound of the present invention will be explained, it should not be restricted thereto.

The compound(I) of the present invention expressed by formula 1 can be manufactured by reaction formula A shown in FIG. 1.

In reaction formula A, the alkylenediamine derivative(I) of the present invention can be obtained from a carboxylic acid(II) and an amine(III) by using a known amide-bond forming reaction such as mixed anhydride method, acid chloride method, DCC method, CDI method, or azide method. Here, W in the compound(II), and $R_4$, $R_5$, $R_6$, n, and Y in the compound (III) are defined as formula 1 mentioned above.

In the mixed anhydride method, by using an activator such as diphenyl phosphinic chloride, ethyl chloroformate, isobutyl chloroformate, or pivaloyl chloride, the carboxylic acid (II) is converted into its corresponding anhydride and then reacted with the compound(III). As an additive, for example, an organic base such as triethyl amine, pyridine, or N-methylmorpholine can be used. As a solvent, for example, a halogenated hydrocarbon such as dichloromethane or chloroform; an aromatic hydrocarbon such as benzene, toluene, or xylene; an ether such as tetrahydrofuran or dioxane; or an amide such as dimethylformamide or dimethylacetamide can be used. While the reaction temperature and reaction time may be changed according to the material compounds used, the reaction is usually effected at a temperature within the range of −15° C. to the reflux temperature of the solvent.

In the acid chloride method, as an activator, for example, phosphorus pentachloride, phosphorus trichloride, or thionyl chloride is used to convert the carboxylic acid (II) into the corresponding acid chloride and then the latter is reacted with the compound (III). As an additive, for example, an organic base such as triethyl amine, pyridine, or N-methylmorpholine can be used. As a solvent, for example, a halogenated hydrocarbon such as dichloromethane or chloroform; an aromatic hydrocarbon such as benzene, toluene, or xylene; or an amide such as dimethyl formamide or dimethylacetamide can be used. While the reaction temperature and reaction time may be changed according to the material compounds used, the reaction is usually effected at a temperature within the range of 0° C. to the reflux temperature of the solvent.

In the DCC method, as a condensing agent, for example, dicyclohexyl carbodiimide (DCC) or 1-ethyl-3-(3-dimethylaminopropyl)carbodiimide hydrochloride (WSCI) can be used. As a solvent, for example, a halogenated hydrocarbon such as dichloromethane or chloroform; an aromatic hydrocarbon such as benzene, toluene, or xylene; an ether such as tetrahydrofuran or dioxane; or an amide such as dimethylformamide or dimethylacetamide can be used. If necessary, this reaction may be effected while 1-hydroxybenzotriazole (HOBt) or N-hydroxy succinimide (HOSu) is added thereto. While the reaction temperature and reaction time may be changed according to the material compounds used, the reaction is usually effected at a temperature within the range of 0° C. to the reflux temperature of the solvent.

In the CDI method, as an activator, for example, N,N'-carbonyldiimidazole is used to convert the carboxylic acid (II) into the corresponding N-acyl derivative and then the latter is reacted with the compound(III). As an additive, for example, an organic base such as triethylamine, pyridine, or N-methylmorpholine or an inorganic base such as sodium hydride or potassium hydride can be used. As a solvent, for example, a halogenated hydrocarbon such as dichloromethane or chloroform; an aromatic hydrocarbon such as benzene, toluene, or xylene; an ether such as tetrahydrofuran or dioxane; or an amide such as dimethylformamide or dimethylacetamide can be used. While the reaction temperature and reaction time may be changed according to the material compounds used, the reaction is usually effected at a temperature within the range of 0° C. to the reflux temperature of the solvent.

In the azide method, as an activator, for example, diphenylphosphorylazide is used to convert the carboxylic acid (II) into the corresponding azide and then the latter is reacted with the compound (III). As an additive, for example, an organic base such as triethylamine, pyridine, or N-methylmorpholine is used. As a solvent, for example, a halogenated hydrocarbon such as dichloromethane or chloroform; an aromatic hydrocarbon such as benzene, toluene, or xylene; an ether such as tetrahydrofuran or dioxane; or an amide such as dimethylformamide or dimethylacetamide can be used. While the reaction temperature and reaction time may be changed according to the material compounds used, the reaction is usually effected at a temperature within the range of 0° C. to the reflux temperature of the solvent.

Specifically, for example, diphenylphosphinic chloride or pivaloyl chloride is used as an activator for the mixed anhydride method, while triethylamine is used as an additive to effect a reaction in a solvent such as chloroform or dimethyl formamide at a temperature within the range of −15° C. to room temperature, thereby attaining the aimed object.

Among the material compound(II) used in reaction formula A, the compound (II-a) wherein W is a group expressed by formula 2 can be synthesized by reaction formula B shown in FIG. 2, for example.

In reaction formula B, m in the compound (IV) represents an integer of 1 to 3. While $R_1$, $R_2$, and X are defined as formula 2 mentioned above, $R_1$=H when m=2, and $R_1$=$R_2$=H when m=3. Ra represents a carboxyl-protecting group which may be a lower alkyl group such as methyl group, ethyl group, or tert-butyl group, phenacyl group, or trichloroethyl group as long as no problem occurs in the subsequent reaction. Z in the compound (V) represents a halogen atom. $R_3$ and $R_3'$ are defined as formula 2 mentioned above.

In reaction formula B, an alkenyl halide(V) is reacted with a compound(IV) in the presence of a base and then hydrolyzed so as to synthesize the carboxylic acid (II-a).

The first step of this reaction can be effected in the presence of a base. Sodium amide, triethylamine, sodium hydride, sodium hydroxide, potassium carbonate, barium oxide, silver oxide, or the like can be used therefor. Also, a catalytic amount of potassium iodide can be added thereto. As a solvent, for example, an alcohol such as methanol, ethanol, or butanol; an aromatic compound such as benzene, toluene, xylene, or pyridine; an ether such as diethylether, tetrahydrofuran, or dioxane; an amide such as dimethylformamide or dimethylacetamide; or a ketone such as dimethylsulfoxide or acetone can be used. While the reaction temperature and reaction time may be changed according to the material compounds used, the reaction is usually effected at a temperature within the range of 0° C. to the reflux temperature of the solvent.

Specifically, for example, the compound (IV) is dissolved in tetrahydrofuran or N,N'-dimethylformamide and, after sodium hydride is added as a base and stirred therein, the alkenyl halide(V) is added thereto so as to effect a reaction at a temperature within the range of room temperature to the reflux temperature of the solvent, thereby attaining the aimed object.

In the reaction of the second step, the ester compound (VI) is hydrolyzed in the presence of an acid or a base so as to synthesize the carboxylic acid (II-a). Hydrochloric acid, sulfuric acid, p-toluenesulfonic acid, or the like can be used as the acid, while sodium hydroxide, potassium hydroxide, potassium t-butoxide, or the like can be used as a base. As a solvent, a carboxylic acid such as formic acid or acetic acid, an alcohol such as methanol or ethanol; water; or a mixed solvent thereof can be used. While the reaction temperature and reaction time can be changed according to the material compounds used, the reaction is usually effected at a temperature within the range of 0° C. to the reflux temperature of the solvent.

Specifically, for example, the ester compound(VI) is dissolved in an alcohol such as methanol or ethanol and then an aqueous sodium hydroxide or potassium hydroxide solution is added thereto so as to effect a reaction at a temperature within the range of room temperature to reflux temperature of the solvent, thereby attaining the aimed object.

The material compound (V) used in reaction formula B can be synthesized by reaction formula C shown in FIG. 3.

In reaction formula C, Z, $R_3$, and $R_3'$ are defined as those in reaction formula B mentioned above. In this reaction formula, an alkenyl halide (V) can be obtained by halogenation of alcohol (VII).

For this reaction, a general method known as halogenation of hydroxy groups can be used. As a reagent of halogenation, for example, a strong acid such as hydrochloric acid or hydrobromic acid; a phosphorus compound such as phosphorus tribromide, phosphorus trichloride, or phosphorus pentachloride; thionyl chloride; N-halogenosuccinimide and methyl sulfide; triphenylphosphine and a halogenated hydrocarbon; or methanesulfonyl chloride and lithium halide is used to effect the reaction. As a solvent, for example, a halogenated hydrocarbon such as dichloromethane or chloroform; an aromatic compound such as benzene, toluene, xylene, or pyridine; an ether such as diethylether, tetrahydrofuran or dioxane; or an amide such as N,N-dimethylformamide or N,N-dimethylacetamide can be used. While the reaction temperature and reaction time may be changed according to the material compounds used, the reaction is usually effected at a temperature within the range of 0° C. to the reflux temperature of the solvent.

Specifically, for example, in the presence of lithium chloride and triethylamine, methanesulfonyl chloride is used so as to effect a reaction in a solvent such as acetone at a temperature within the range of 0° C. to room temperature, thereby attaining the aimed object.

Among material compounds(II) used in reaction formula A, the compound (II-b) wherein W is a group expressed by formula 3 above-mentioned can be synthesized according to reaction formula D shown in FIG. 3, for example.

At the first step of reaction formula D, the compound (XVII) is reacted with the substituted benzyl halide(XVIII) in the presence of a base to obtain the compound (XIX). $R_{10}$ in the compound (XVII), and $R_{11}$ in the compound (VIII) are defined as those of formula 3 mentioned above, while Z in the compound (XVIII) represents a halogen atom. Ra in the compound (XVII) represents a carboxyl-protecting group which may be a lower alkyl group such as methyl group, ethyl group, or tert-butyl group, phenacyl group, or trichloroethyl group as long as no problem occurs in the subsequent reaction.

As a base in this reaction, for example, an inorganic base such as potassium carbonate, potassium hydroxide, sodium hydroxide, or sodium hydride; or an organic base such as triethylamine or pyridine can be used. Specifically, for example, potassium carbonate is used as a base so as to effect a reaction in a solvent such as acetone or N,N-dimethylformamide at a temperature within the range of room temperature to the reflux temperature of the solvent, thereby attaining the aimed object.

At the second step of reaction formula D, the compound (XIX) is subjected to a deprotecting reaction so as to obtain the carboxylic acid(II-b).

For this deprotecting reaction, various kinds of known methods can be used according to the kind of the protecting group Ra. For example, when Ra is methyl or ethyl group, known ester hydrolysis method is used for deprotection. Specifically, for example, an inorganic base such as sodium hydroxide or potassium hydroxide is used so as to effect a reaction in a solvent such as water, methanol, or ethanol at a temperature within the range of room temperature to the reflux temperature of the solvent, thereby attaining the aimed object.

On the other hand, among the material compounds(III) used in reaction formula A, for example, the compound (III-a) wherein n=2 and $R_4$=H can be synthesized according to reaction formula E shown in FIG. 5.

In reaction formula E, a halogenoacetonitrile (IX) is reacted with an amine (VIII) in the presence of a base and then the cyano group is reduced so as to synthesize the ethylenediamine (III-a). Here, in the compound (VIII), $R_5$, $R_6$, and Y are defined as those in formula 1. Z in the compound (IX) represents a halogen atom.

At the first step of this reaction, the reaction can be effected under a reaction condition similar to that of the first step in reaction formula B.

For reduction of the cyano group at the second step in this reaction, a known method can be used. For example, Birch reduction method, a reduction method by a metal hydride complex compound, or a method using Raney nickel can be used. In Birch reduction, while sodium or lithium is used mainly as a catalyst, the reaction can be effected in the mixed solvent of liquid ammonia and an alcohol such as methanol or ethanol. When the metal hydride complex compound is used, lithium aluminium hydride, aluminium hydride, sodium borohydride, or the like can be used as a reagent. As a solvent, for example, an ether such as diethylether, tetrahydrofuran or dioxane; or an alcohol such as methanol, ethanol, or butanol can be used. When sodium borohydride is used, Raney nickel, aluminium chloride, cobalt chloride, or the like can be used as a catalyst. When Raney nickel is used, methanol saturated by ammonia is used as a solvent so as to effect hydrogenation under a pressure, thereby attaining the aimed object. While the reaction temperature and reaction time may be changed according to the material compounds used in all cases, the reaction is usually effected at a temperature within the range of 0° C. to the reflux temperature of the solvent.

Specifically, for example, lithium aluminium hydride is suspended in tetrahydrofuran while being cooled with ice and, after the compound (X) is dropped thereto, the reaction is effected at a temperature within the range of 0° C. to the reflux temperature of the solvent. Then, the reaction solution is treated with water, an aqueous sodium hydroxide solution, or the like, thereby attaining the aimed object.

Also, among the material compound(III) used in reaction formula A, the compound(III-b) wherein n=2 and $R_4$ is a lower alkyl group can be synthesized according to reaction formula F shown in FIG. 6.

In reaction formula F, ethylenediamine (III-a) is amidated with the compound (XI) and then the ketone group in the amide bond is reduced so as to synthesize the ethylenediamine (III-b). Here, in the compound (III-a), $R_5$, $R_6$ and Y are defined as those in formula 1 mentioned above. In the compound (XI), $R_8$ represents hydrogen atom or a lower alkyl group, while A represents hydroxy group or —$OCOR_8$.

The amidation at the first step of this reaction can be effected under a reaction condition similar to that in reaction formula A.

In the reaction at the second step, as a reducing reagent, for example, lithium aluminium hydride, aluminium hydride, or sodium borohydride and triethyloxonium tetrafluoroborate can be used. As a solvent, for example, a halogenated hydrocarbon such as dichloromethane or chloroform; an aromatic compound such as benzene, toluene, xylene, or pyridine; an alcohol such as methanol, ethanol, or butanol; or an ether such as diethylether, tetrahydrofuran or dioxane can be used. While the reaction temperature and reaction time may be changed according to the material compounds used in all cases, the reaction is usually effected at a temperature within the range of 0° C. to the reflux temperature of the solvent.

Specifically, for example, lithium aluminium hydride is suspended in tetrahydrofuran while being cooled with ice and, after the amide compound (XII) is dropped thereto, the reaction is effected at a temperature within the range of 0° C. to the reflux temperature of the solvent. Then, the reaction solution is treated with water, an aqueous sodium hydroxide solution, or the like, thereby attaining the aimed object.

Among the material compound(VIII) used in reaction formula E mentioned above, the compound (XVI) wherein Y is a group expressed by —$N(R_7)$— can be synthesized according to reaction formula G shown in FIG. 7.

In reaction formula G, $R_9$ in the compound (XIII) represents an amino-protecting group which can be a urethane type protecting group such as benzyloxycarbonyl group or tert-butyloxycarbonyl group, an acyl type protecting group such as formyl group or tosyl group, or an alkyl type protecting group such as trityl group as long as no problem occurs in the subsequent reaction. $R_5$ and $R_6$ in the compound (XIII), and $R_7$ in the compound (XIV) are defined as those in formula 1 mentioned above, while Z represents a halogen atom.

At the first step of reaction formula G, the protected piperazine (XIII) is reacted with an appropriate halide (XIV) in the presence of a base so as to obtain the compound (XV). This reaction can be effected under a reaction condition similar to that of the first step in reaction formula B.

At the second step of reaction formula G, the compound (XV) is subjected to a deprotecting reaction so as to obtain the compound (XVI). For this deprotecting reaction, various kinds of known methods can be used according to the kind of the amino-protecting group $R_9$. For example, hydrazine, hydrochloric acid, hydrogen peroxide, or the like can be used as the deprotecting agent when $R_5$ is formyl group. Specifically, for example, hydrochloric acid within the range of 1N to 6N is used to effect the reaction in methanol at a temperature within 0° C. to room temperature, thereby attaining the aimed object.

Among the material compounds used in the above-mentioned reaction formulas A to G, those with no preparation methods described may be commercially available or easily synthesized by using a known method.

Also, examples of salts of the alkylenediamine derivative of the present invention (I) with an acid include salts with inorganic acids such as hydrochloric acid, hydrobromic acid, sulfuric acid, and phosphoric acid and salts with organic acids such as acetic acid, propionic acid, citric acid, lactic acid, oxalic acid, maleic acid, fumaric acid, succinic acid, tartaric acid, and methane sulfonic acid. These salts can be easily manufactured by a normal method.

The alkylenediamine derivative in accordance with the present invention has a strong effect against stress ulcer and an excellent effect for suppressing gastric acid secretion. Further, it has an antibacterial activity against *Helicobacter pyroli* which is supposed to be a cause for recurrence of ulcer. Furthermore, it has a high safety. Accordingly, it is useful as a medicament for curing and preventing peptic ulcer in man or mammals and, particularly, gastric ulcer in man. Conventionally, there has hardly been known such a compound which has both effect for suppressing gastric acid secretion and antibacterial activity against *Helicobacter pyroli*. Accordingly, it is indicated that the compound of the present invention is not only effective in preventing and curing ulcer but also in preventing the recurrence thereof.

When the compound of the present invention is administered as a medicament for curing and preventing peptic ulcer, it may be administered orally as tablet, powder, granule, capsule, syrup, or the like as well as parenterally as suppository, injection, external drug, instillation or the like. While the amount of administration may be outside of the range mentioned below according to the degree of symptom, personal difference, age, kind of ulcer, or the like, it should of course be adjusted so as to fit the individual circumstances in specific cases. Usually 0.01 to 200 mg/kg or, preferably, 0.05 to 50 mg/kg or, more preferably, 0.1 to 10 mg/kg is administered per day for an adult in a single dose or several doses.

When formulating the medicament, a normal manufacturing method is used with a normal formulation carrier. If necessary, pharmacologically and pharmaceutically acceptable additives may be added thereto.

Namely, when preparing an oral solid formulation, after an excipient and, if necessary, a binder, a decaying agent, a luster, a coloring agent, a correctives, and the like are added to the main medicament, a normal method is used to form tablet, coated tablet, granule, powder, capsule, or the like.

Examples of the excipient include lactose, corn starch, sucrose, glucose, sorbitol, crystalline cellulose, and silicon dioxide. Examples of the binder include polyvinylalcohol, polyvinylether, ethyl cellulose, methyl cellulose, gum arabic, tragacanth, gelatin, shellac, hydroxypropyl cellulose, hydroxypropyl starch, and polyvinylpyrrolidone. Examples of the decaying agent include starch, agar, gelatin powder, crystalline cellulose, calcium carbonate, sodium hydrogencarbonate, calcium citrate, dextrin, and pectin. Examples of the luster include magnesium stearate, talc, polyethyleneglycol, silica, and hardened vegetable oil. As the coloring agent, those permitted to be added to medicines are used. Examples of the correctives include cocoa powder, menthol, aromatic acid, mentha oil, borneol, and cinnamon powder. If necessary, these tablet and granule can be coated with sugar-coating, gelatin-coating, and the like.

When preparing an injection, if necessary, a pH-adjusting agent, a buffer, a stabilizer, a solubilizer, and the like are added to the main medicament and then a normal method is used to form subcutaneous, intramuscular, and intravenous injection drugs.

In the following, the present invention will be explained in further detail by specifically examples. However, the present invention should not be restricted to these examples.

First, test methods used for evaluating these examples will be explained.

WIS: Restraint and Water Immersion Stress-Induced Ulcer Inhibition Test i) Meaning The degree of inhibition of the stress ulcer formation is tested.

ii) Method

Male Crj:SD or Slc:SD rats (6 to 7-week-old) were fasted overnight, but allowed free access to water. Each group has 5 to 8 of these rats. The sample compound was dissolved or suspended in an aqueous solution of 0.3% sodium carboxymethylcellulose or 0.05% Tween 80 and then was orally administered (100 mg/10 ml/kg). To a control group, the vehicle was administered. 10 minutes later, the rats were placed in a stress cage and immersed to the level of xipfoid process in a water bath (21° C.) for 7 hours. At the end of the stress, the rats were sacrificed by inhalation of ether or carbon dioxide. Then, the stomach of each was removed, inflated by injecting 10 ml of 5% formalin neutral buffer solution, and immersed in 1% formalin neutral buffer solution for 30 minutes or more to be fixed. The stomach was incised along the greater curvature and then the length of each erosion in the glandular portion was determined under dissecting microscope. The sum of the length of erosions per stomach was defined as ulcer index (UI).

iii) Judgment Standard

The effect obtained when 100 mg/kg of the sample compound had been administered was expressed as ulcer formation inhibitory rate (%) as follows:

ulcer formation inhibitory rate (%) =

$$(1 - (UI \text{ in sample group}/UI \text{ in control group})) \times 100$$

VOL, TAO: Acid Secretion Inhibition Test In Vivo i) Meaning

Inhibitory effect on acid secretion in vivo is confirmed.

ii) Method

Male Crj:Donryu rats (7-week-old) were fasted overnight but allowed free access to water. In each group, 8 to 10 of these rats were used under urethane anesthesia (1.25 g/kg). The sample compound dissolved or suspended in an aqueous solution of 0.5% sodium carboxymethylcellulose or 0.05% Tween 80 was orally administered (100 mg/10 ml/kg). 30 minutes later, the abdomen of each was incised and the pylorus was ligated. 30 minutes after the ligation, 30 mg/kg of histamine dissolved in physiological saline was subcutaneously administered and, 3 hours thereafter, the rat was sacrificed with carbon dioxide. Immediately thereafter, each stomach was removed and the gastric contents were collected and each volume was determined. The total acid output was determined by titration of the gastric juice with 0.1N NaOH.

iii) Judgment Standard

With respect to the gastric juice volume (VOL) and the total acid output (TAO), the effects obtained when 100 mg/kg of the sample compound had been administered were expressed as their respective inhibitory rates (%) as follows:

each inhibitory rate (%) =

$$(1 - (\text{value in sample group}/\text{value in control group})) \times 100$$

CAP: Acid Secretion Inhibition Test In Vitro i) Meaning

The acid secretion inhibitory activity in a cell level is studied. It can also be used for studying the mechanism of the effect.

ii) Method ii-a) Preparation of isolated gastric fundus gland suspension

First, an isolated gastric fundic gland sample was prepared. Namely, a male Japanese White rabbit (2.5 to 3 kg) was anesthetized to death with Nembutal™ and then the abdomen was incised. Immediately thereafter, the stomach was removed and, after its pyloric and cardiac antrum were severed, incised along its greater curvature into two sheets. The gastric contents adhering to the mucosal surface was washed out with ice-cooled PBS (-) and then carefully washed therein. The gastric wall was spread on a cork board with its mucosal surface facing up and the feed and mucus thereon were completely removed with sterile gauze. The mucosa was separated therefrom by a spatula and then collected in ice-cooled PBS (-). After being washed twice with PBS (-), the mucosa was minced into 2–3 $mm^3$ pieces by scissors. These pieces were further washed twice with a nutrient solution. The nutrient solution comprises 132.4 mM of NaCl, 5.4 mM of KCl, 5 mM of $Na_2HPO_4.12H_2O$, 1 mM of $NaH_2PO_4.2H_2O$, 1.2 mM of $MgSO_4$, 1 mM of $CaCl_2$, 25 mM of HEPES, 2 mg/ml of glucose, and 1 mg/ml of BSA. Into 70 ml of the nutrient solution containing 1 mg/ml of collagenase, minced mucosal pieces were dispersed and intensely stirred in a conical flask with a stirrer at 37° C. for 40 to 60 minutes. During this period, 100% $O_2$ was sprayed on the nutrient solution surface and the pH was appropriately measured such that it was immediately adjusted to pH 7.4, when the value was therebelow, with a base. The nutrient solution was added to the reaction solution so as to attain the total amount of about 200 ml. After being filtered through a mesh, the suspension was divisionally introduced into 50 ml centrifuge tubes and left for 15 minutes such that gastric fundic gland was deposited. The supernatant was repeatedly removed by an aspirator, dispersed in the nutrient solution, and then left such that the gastric fundic gland was washed three times. At this time, without using a pipette, the suspension was alternately introduced into two centrifuge tubes so as to effect dispersion. The number of cells was counted under microscope and adjusted to $1.6 \times 10^6$ cells/ml.

ii-b) [$^{14}$C]-aminopyrine uptake test

Then, [$^{14}$C]-aminopyrine uptake test was performed. After an Eppendorf tube was weighed, 10 µl (final concentration: $10^{-5}$M) of histamine dissolved in the above-mentioned nutrient solution, 10 µl (final concentration: $10^{-5}$M) of the test compound dissolved in DMSO, and 10 µl (final concentration: 0.05 µCi/ml) of [$^{14}$C]-aminopyrine diluted with the nutrient solution were introduced therein and then 970 µl of the isolated gastric fundic gland suspension prepared above was added thereto. Subsequently, this mixture was shaken at 37° C. for 40 minutes at 125 cycles/minute. After being centrifuged for 30 minutes, 200 µl of its supernatant was collected into a mini-vial, while the rest was removed by an aspirator. The gland pellet was completely dried as the tube with its lid being opened was kept for one night in a drying oven at 80° C. and then the lid was closed and the weight was determined at room temperature. Then 100 µl of 1N KOH was added thereto and the tube with its lid being closed was treated at 60° C. for 1 to 2 hours so as to dissolve the pellet. Then, the contents thereof were transferred to a mini-vial. Into the mini-vial containing the supernatant or gland pellet, 4 ml of Atomlite™ was added and then the radioactivity was measured by a liquid scintillation counter. Here, after the radioactivity of the gland pellet was corrected by using a sample in which 20 mM of NaSCN was added so as to cancel the hydrogen ion concentration gradient, the integration ratio of aminopyrine specifically trapped by the gland pellet was calculated. This experiment was performed in duplicate.

ii-c) Calculation of the accumulation rate of aminopyrine

Here, its principle will be briefly explained. In the isolated gastric fundic gland, acid is accumulated in a space between its secretory tubule and intraglandular cavity. Aminopyrine is weak base (pKa=5.0) and nonionic in a neutral solution so as to freely pass through the cell membrane, whereas it is ionized in an acidic solution and thus cannot pass through the cell membrane due to its electric charge. Therefore, aminopyrine is accumulated in a closed acidic space within the isolated gastric fundic gland. In view of this characteristic, the accumulation rate (R) of aminopyrine is calculated by the following equation:

$R$ = ((corrected radioactivity of precipitate)/(radioactivity of supernatant)) ×

(200/(mg dry weight of gland pellet))

iii) Judgment Standard

The effect of the sample compound at the final concentration of $10^{-5}$M was expressed by acid secretion inhibitory rate (%) as follows:

acid secretion inhibitory rate (%) =

-continued (1 − ($R$ in sample group/$R$ in control group)) × 100

AHP: Antibacterial Activity Test Against *Helicobacter pyroli* i) Meaning

The minimum inhibitory concentration (MIC) against *Helicobacter pyroli* (microaerophilic gram-negative bacterium which is supposed to deeply involve in pathogenesis, relapse, and recrudescence of ulcer, referred to as "HP" in the following) is measured so as to find out compounds which have antimicrobial activity against *Helicobacter pyroli*.

ii) Method

MICs were determined by the agar dilution method. The stock culture (−80° C.) of HP NCTC 11637 was thawed and cultured on tripticase soy agar supplemented with 5% sheep blood at 37° C. in an atmosphere of 5% $O_2$, 10% $CO_2$, and 85% $N_2$. Grown colonies were transferred to the same plate and precultured for 3 days under the same condition. An appropriate amount of the colony grown on the plate by preculturing was suspended in Mueller Hinton broth till turbidness was recognizable by naked eyes, and diluted 100-fold in the same broth; this resulted in a bacterial suspension for inoculation containing about $10^5$ cfu/ml of the bacteria.

A 1,000 µg/ml solution of the sample compound containing DMSO not more than 25% was serieslly diluted 2-fold in sterile purified water. 100 µl volume from each dilution was mixed thoroughly with 900 µl of brucella agar supplemented with 5% horse blood and solidified in a 24 well micro plate, thereby yielding an MIC measurement plate.

10 µl of the bacterial suspension for inoculation (about $10^3$ cfu) was inoculated on this plate and cultured for 7 days under the same condition as that of preculture. Thereafter, it was judged whether there had been bacteria growth or not.

iii) Judgment Standard

The minimum concentration of the sample compound when there were no visible colonies or, if any, 5 or less colonies of HP was defined as MIC (µg/ml).

PD: Gastric Mucosal Integrity Test i) Meaning

There is a possibility that the anti-ulcer mechanism of the compounds which were effective in the experimental ulcer model may be attributed to adaptive cytoprotection, which means exhibiting of apparent anti-ulcer effect due to increase in the amount of endogenous prostaglandins in the gastric mucosa caused by necrotizing agents. In this case, since the sample compound has a necrotizing effect, it is inappropriate as an anti-ulcer medicament.

Therefore, the gastric mucosal potential difference (PD), which reflects the integrity of the gastric mucosa, is measured so as to confirm that the sample compound has no damaging effect on gastric mucosa, which is toxicity at gastric mucosal level.

ii) Method

Male Crj:SD rats (7 to 8-week-old) were fasted overnight, but allowed free access to water, and then, under urethane anesthesia (1.25 g/kg, i.p.), fixed to a cork board on its back. The abdomen of each rat was incised, and a small incision was made in the forestomach. Then, the inside of the stomach was washed with physiological saline heated at 37° C. From the forestomach, along the greater curvature thereof, the stomach was incised without damaging blood vessels. After the height of the cork board was adjusted on a jack, the stomach was mounted on ex vivo chamber. The area of the gastric mucosa exposed to the inside of this chamber was 2.5 cm². The inside of the chamber was perfused with physiological saline warmed at 37° C. by micro tube pump. By using an agar bridge containing 3M KCl, the potential difference between the chamber and the abdominal cavity was measured by a PD meter. Here, the rectal temperature was measured to control the body temperature during the experiment. After the PD was sufficiently stabilized, the perfusate was stopped and then 100 mg/10 ml/kg of the sample compound dissolved or suspended in an aqueous solution of 0.5% sodium carboxymethyl cellulose or 0.05% Tween 80 was administered into the chamber, while PD was recorded for 60 minutes. To a control, the vehicle was administered.

iii) Judgment Standard

The change in PD during 60 minutes after the administration of 100 mg/kg of the sample compound was collectively studied and, with reference to the positive control, classified into 5 levels as follows:

5: Same as the control with no recognizable damage at all.

4: Though a slight PD-decreasing tendency suggesting a slight possibility of mucosal damage is found, there is no problem.

3: Though a weak decrease in PD and a possibility of a weak mucosal damage is recognized, there is no substantial problem.

2: Medium degree of decrease in PD is found and a mucosal damage is recognized.

1: Heavy degree of decrease in PD is found and a remarkable mucosal damage is recognized.

AT: Single Dose Toxicity Pretest i) Method

Male Slc:ICR mice (5-week-old) were used. Each group has 3 to 5 mice and each mouse was fasted, but allowed free access to water, for 4 to 5 hours from 9 a.m. in the test day. Then, 2,000 mg/10 ml/kg of the sample compound dissolved or suspended in an aqueous solution of 0.5% sodium carboxymethyl cellulose was orally administered thereto. To a control, only the vehicle was administered. The behavior and symptom were observed at each of 15 minutes, 30 minutes, 1 hour, 2 hours, and 3 hours after the administration and then daily till one week thereafter. The body weight was measured before and after the fasting as well as at the same time everyday. The dead animals were immediately subjected to autopsy and their organs were observed microscopically. Also, the living animals were sacrificed with ether or carbon dioxide one week after the administration and then their organs were observed microscopically.

ii) Judgment Standard

The toxicity at the single dose of 2,000 mg/kg of the sample compound was expressed as being classified into 5 levels.

5: Mortality rate is 0%; no toxicity is found at all both in behavior and organs.

4: Mortality rate is 0%; while no toxicity is found in organs, slight toxicity is observed in behavior and body weight increase.

3: While there is a dead animal (though not all the animals are dead), no toxicity is found in organs.

2: Regardless of whether there is a dead animal or not, toxicity is found in organs.

1: All the animals are dead.

MTT: Cell Damaging and Protecting Effect Test i) Meaning

It is confirmed that there is no toxicity in cell level. Those having a toxicity in cell level are inappropriate as an anti-ulcer drug. Also, it can be confirmed that the effects of the sample compounds in other cell level tests do not result from their toxicity.

ii) Method

A male Japanese White rabbit (2.5 to 3 kg) was anesthetized to death by Nembutal™ and, immediately thereafter, its stomach was removed. The greater curvature of the stomach was incised so as to remove the stomach contents therefrom. After the mucosal surface was washed with HBSS (Hanks' Balanced Salt Solution), the stomach in ice-cooled HBSS was transferred to a laboratory. Then, after the pyloric antrum was removed, the gastric corpus mucosa was separated by a spatula and then minced into 2 to 3 mm³ pieces in BME (Basal Medium Eagle). Thereafter, these pieces were shaken at 120 to 130 cycles/minute for 15 minutes at 37° C. in BME 60 ml containing 280 U/ml of dispase and 30 to 50 U/ml of collagenase. Here, the concentration of collagenase was appropriately changed for each lot in view of the state of cells. The pieces were washed twice with EBSS (Earle's Balanced Salt Solution) containing 1 mM of EDTA and then shaken in MEM (Minimum Essential Medium) containing 1 mM of EDTA at 37° C. for 5 minutes. Subsequently, they were shaken in the dispase and collagenase having the same concentrations as those mentioned above for 15 minutes so as to remove the supernatant and then further shaken at 37° C. for 50 to 60 minutes at 120 to 130 cycles/minute. Then, after being washed twice with HBSS, Ham F12 containing 2% of Ultrocer G™ was used to attain the concentration of $1 \times 10^6$ cells/ml. Thus formed suspension was dispensed in each well of a 96-well plate by 200 µl. The plate was incubated in the atmosphere composed of 5% $CO_2$ and 95% air at 37° C. for three days so as to attain a confluent state and then subjected to MTT assay.

The sample compound was dissolved in DMSO so as to attain a concentration of $10^{-2}$M and then diluted with HBSS containing 2% of Ultrocer G™ so as to attain a final concentration of $10^{-4}$M. To each group, which 8 wells were used for, 10 µl of MTT reagent was added immediately after 100 µl of the medium in each well was exchanged for same volume of the resulting solution of the sample compound. After being incubated in an atmosphere composed of 5% $CO_2$ and 95% air at 37° C. for 4 hours, thus formed solution was centrifuged and then its supernatant was discarded. Subsequently, 100 µl of 100% ethanol was added to the residue so as to dissolve MTT formazan. Then, the absorbance (OD: 570 to 630) was measured by a microplate reader. This method utilizes a phenomenon in which MTT is changed to MTT formazan only by mitochondria of living cells so as to change color.

iii) Judgment Standard

The cell damaging or cell protecting effect of the sample compound at the final concentration of $10^{-4}$M was expressed as cell damaging rate (%) as follows:

cell damaging rate (%) =

(1 − (absorbance in sample group/absorbance in control group)) × 100

Accordingly, the smaller value is better in the cell damaging rate.

Based on the foregoing effect tests and safety tests, the effect and safety of the example compounds of the present invention were studied.

Compound Group 1-1

This compound group has a structure expressed by formula 4 mentioned above, and wherein $R_1$ and $R_2$ are hydrogen atoms. As the alkylenediamine derivatives corresponding to this compound group 1-1, the following compounds were tested. The results of their effect tests and safety tests are shown in Table 1.

Example 1:
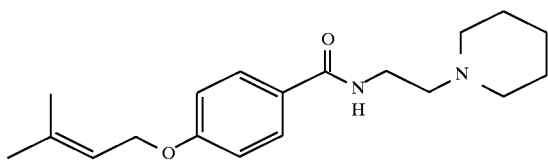
Example 2:
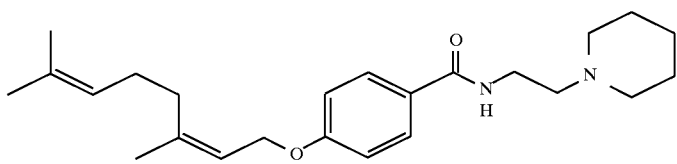
Example 3:
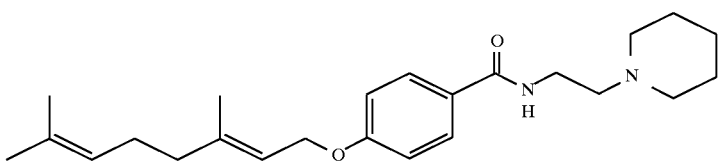
Example 4:
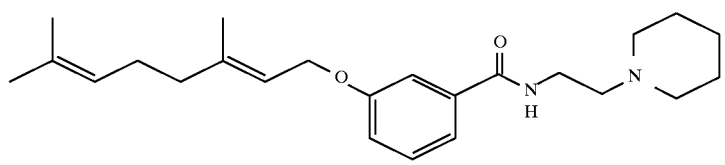
Example 5:
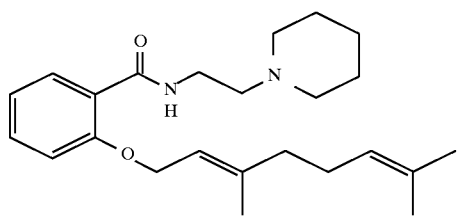
Example 6:
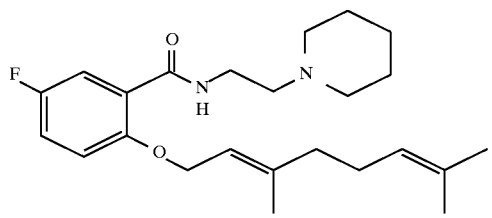
Example 7:
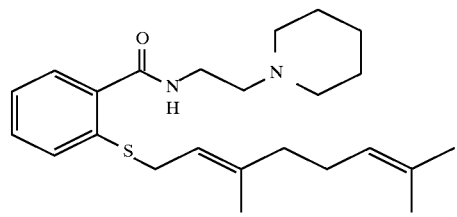

Example 8:

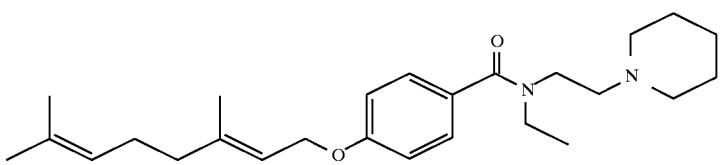

Example 9:

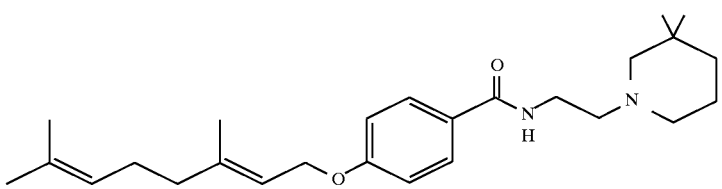

Example 10:

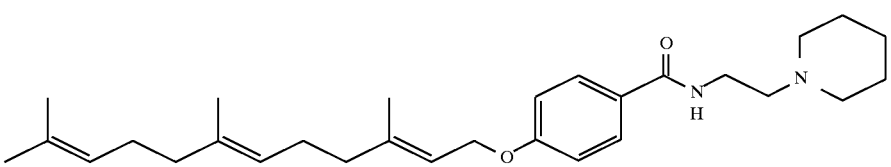

As clearly from Table 1, a compound of this compound group 1-1 has an excellent anti-ulcer effect and acid secretion inhibition effect.

Here, in this compound group 1-1, the bond position of the alkenyloxy group on the aromatic ring has a high degree of freedom. With respect to X, for example, as can be seen from Example 5 and Example 7, even when oxygen atom at X is substituted with sulfur atom, the effect has been maintained. Also, for example, from Example 5 and Example 6, it has been suggested that even when hydrogen atom at $R_1$ is substituted with fluorine atom, the effect has been maintained.

Further, from Example 3 and Example 8 to 9, it has been shown that even when hydrogen atom at $R_4$, $R_5$, or $R_6$ is substituted with a lower alkyl group, a sufficient effect can be obtained.

TABLE 1

| Example No. | Anti-ulcer Tests | | | | Tests for Safety | | |
|---|---|---|---|---|---|---|---|
| | WIS | VOL | TAO | CAP | PD | AT | MTT |
| 1 | 67 | | | | | | 1 |
| 2 | 79 | | | | | 3 | |
| 3 | 79 | 68 | 85 | 100 | | 4 | |
| 4 | 84 | | | | | 3 | |
| 5 | 78 | | | | | | 21 |
| 6 | 80 | | | | | 3 | 16 |
| 7 | 87 | | | | | | |
| 8 | 67 | | | 100 | | | 41 |
| 9 | 67 | | | | | | |
| 10 | 47 | | | 98 | 5 | 4 | |

Compound Group 1-2

While in the compound group 1-1 mentioned above $R_1$ and $R_2$ are hydrogen atoms, an alkylenediamine derivative in accordance with this compound group 1-2 has a basic structure wherein at least one of $R_1$ and $R_2$ in formula 4 mentioned above is an alkenyloxy group expressed by formula 5 mentioned above. As the alkylenediamine derivatives corresponding to this compound group 1-2, the following compounds were tested. The results are shown in Table 2.

Example 11:

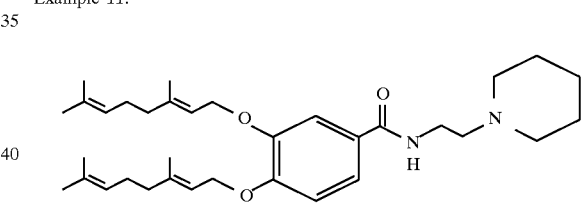

Example 12:

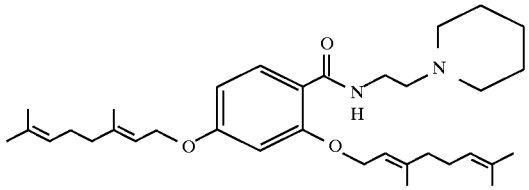

Example 13:

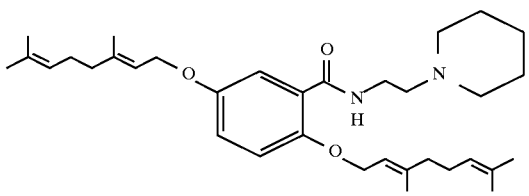

Example 14:

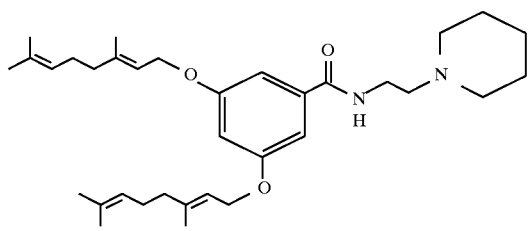

Example 15:

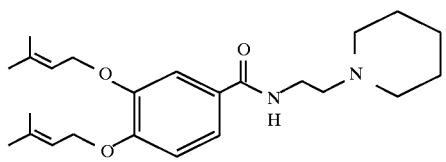

Example 16:

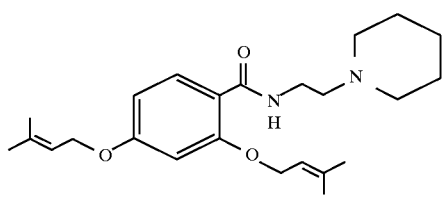

Example 17:

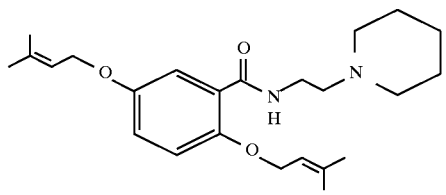

Example 18:

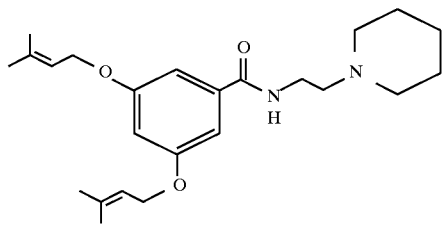

Example 19:

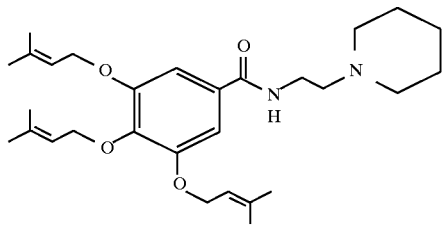

As clearly from Table 2, even when $R_1$ and/or $R_2$ is an alkenyloxy group, a sufficient anti-ulcer effect and acid secretion inhibition effect can be obtained. Also, they are excellent in safety.

Here, in this compound group, the bond position of the alkenyloxy group can be selected with a high degree of freedom, whereby it can bond to various bond position.

TABLE 2

| Example No. | Anti-ulcer Tests | | Tests for Safety | | |
|---|---|---|---|---|---|
| | WIS | CAP | PD | AT | MTT |
| 11 | 91 | | 5 | 4 | 23 |
| 12 | 75 | | | | 38 |
| 13 | 67 | 100 | | 5 | −5 |
| 14 | 66 | | | 3 | 26 |
| 15 | 89 | | | | 17 |
| 16 | 59 | | | | 18 |
| 17 | 70 | 100 | | 3 | −16 |
| 18 | 40 | | | | 33 |
| 19 | 57 | | | 4 | |

Compound Group 1-3

An alkylenediamine derivative of this compound group 1-3 has a basic structure expressed by formula 4 mentioned above, and wherein at least of $R_1$ and $R_2$ is a lower alkoxy group.

As the alkylenediamine derivatives corresponding to this compound group 1-3, the following compounds were tested. The results are shown in Table 3.

Example 20:

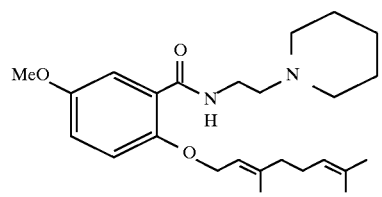

Example 21:

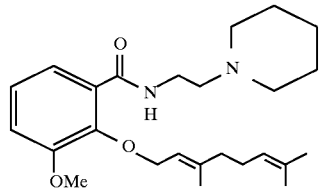

Example 22:

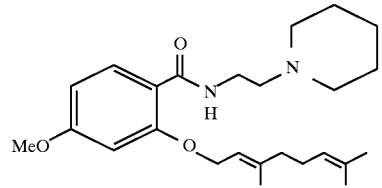

Example 23:

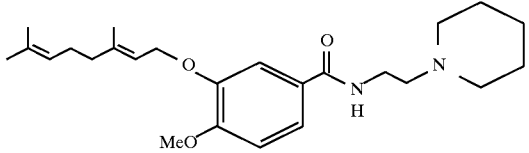

Example 24:

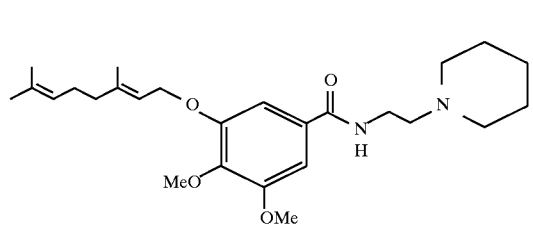

Example 25:

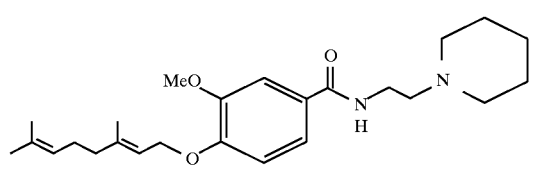

Example 26:

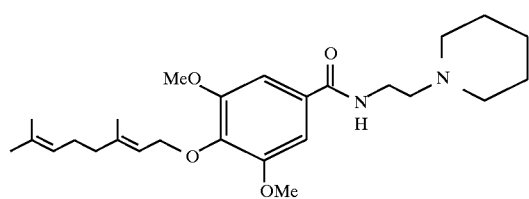

Example 27:

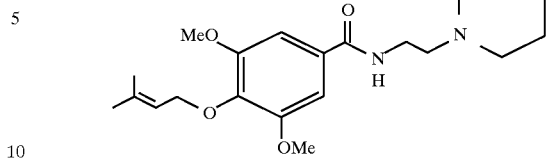

As clearly from Table 3, even when $R_1$ and/or $R_2$ is a lower alkoxy group, a sufficient anti-ulcer effect can be obtained. Especially, from Example 23 and 24, or from Example 25 and 26, it is suggested that when $R_1$ and $R_2$ are lower alkyl groups, more anti-ulcer effect and acid secretion inhibition effect can be obtained.

TABLE 3

| Example No. | Anti-ulcer Test WIS | Tests for Safety | | |
|---|---|---|---|---|
| | | PD | AT | MTT |
| 20 | 71 | | 3 | 35 |
| 21 | 68 | | | 12 |
| 22 | 39 | | | 44 |
| 23 | 56 | | 3 | 43 |
| 24 | 72 | | 5 | 30 |
| 25 | 44 | | 3 | 48 |
| 26 | 72 | | | 17 |
| 27 | 82 | 5 | | −11 |

Compound Group 2-1

An alkylenediamine derivative in accordance with this compound group 2-1 has a basic structure expressed by formula 6 mentioned above, and wherein $R_1$ and $R_2$ are hydrogen atoms. As the alkylenediamine derivatives corresponding to this compound group 2-1, the following compounds were tested.

Example 28:

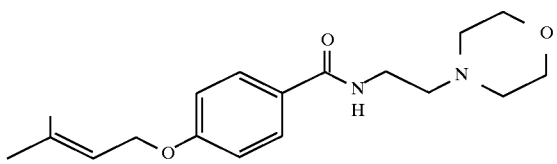

Example 29:

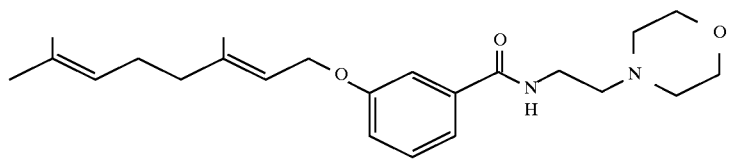

Example 30:

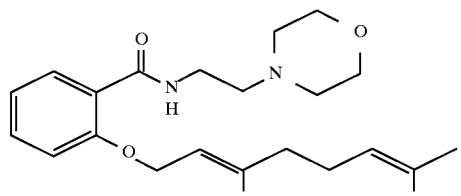

Example 31:

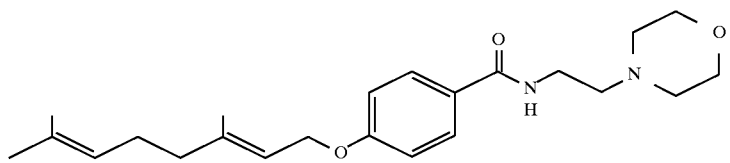

Example 32:

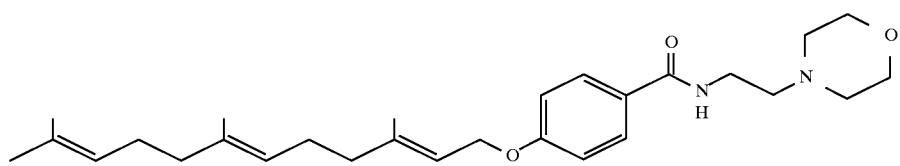

Example 33:

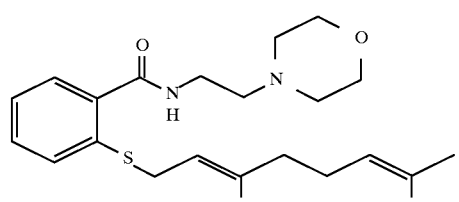

Example 34:

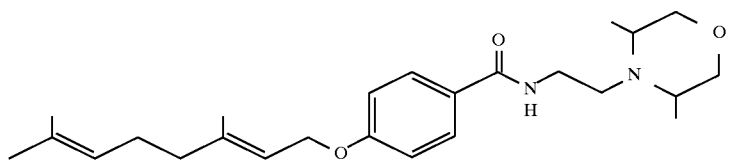

TABLE 4

| Example No. | Anti-ulcer Tests | | Tests for Safety | | |
|---|---|---|---|---|---|
| | WIS | CAP | PD | AT | MTT |
| 28 | 64 | 88 | 5 | 3 | −39 |
| 29 | 63 | 99 | | 5 | 16 |
| 30 | 68 | | | | |
| 31 | 54 | 99 | 3 | 5 | 15 |
| 32 | 55 | 99 | | 5 | 58 |
| 33 | 49 | 100 | | | 5 |
| 34 | 38 | | | | 14 |

As clearly from Table 4, even in this compound group 2-1 in which Y is —O—, a high anti-ulcer effect and acid secretion inhibition effect can be obtained.

Here, in this compound group, as Example 33 and Example 34, it is able to make oxygen atom at X into sulfur atom or to make $R_5$ and $R_6$ into lower alkyl groups.

Compound Group 2-2

While in the compound group 2-1 mentioned above $R_1$ and $R_2$ are hydrogen atoms, an alkylenediamine derivative in accordance with this compound group 2-2 has a basic structure wherein at least one of $R_1$ and $R_2$ in formula 6 mentioned above is an alkenyloxy group expressed by formula 5 mentioned above.

As the alkylenediamine derivatives corresponding to this compound group 2-2, the following compounds were tested. The results are shown in Table 5.

Example 35:

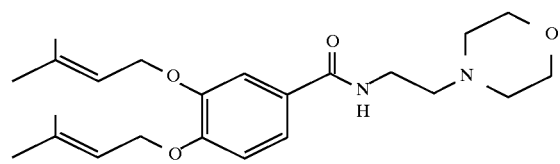

Example 36:

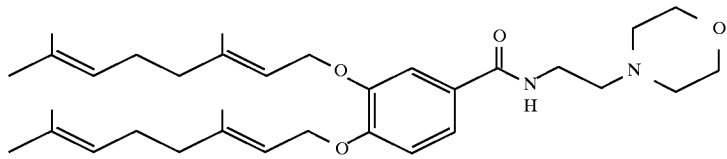

Example 37:

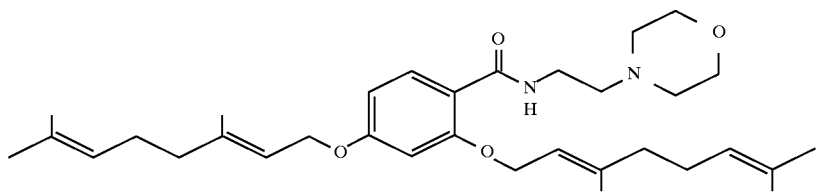

Example 38:

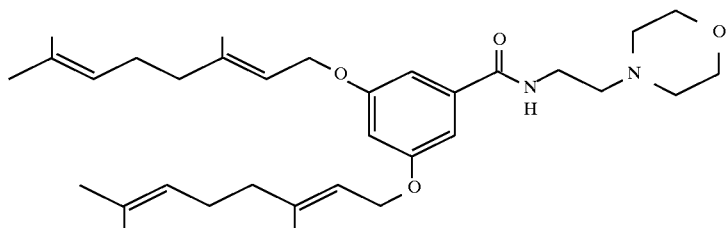

Example 39:

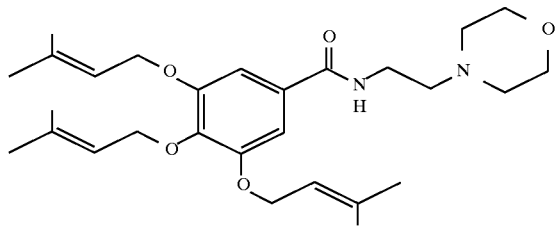

TABLE 5

| Example | Anti-ulcer Tests | | Tests for Safety | | |
|---|---|---|---|---|---|
| No. | WIS | CAP | PD | AT | MTT |
| 35 | 48 | 100 | 5 | 4 | −17 |
| 36 | 39 | | | | |
| 37 | 71 | | | | |
| 38 | 55 | | | | −12 |
| 39 | 76 | | | 4 | |

As clearly from Table 5, even when $R_1$ and/or $R_2$ is an alkenyloxy group, an anti-ulcer effect and acid secretion inhibition effect can be obtained. Also, they are excellent in safety.

Compound Group 3

An alkylenediamine derivative of this compound group 2-3 has a basic structure expressed by formula 6 mentioned above, and wherein at least of $R_1$ and $R_2$ is a lower alkoxy group.

As the alkylenediamine derivatives corresponding to this compound group 2-3, the following compounds were tested.

Example 40:

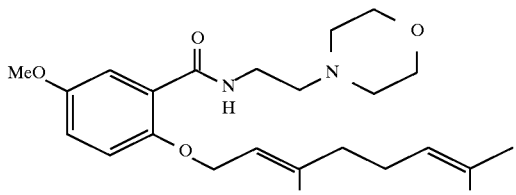

Example 41:

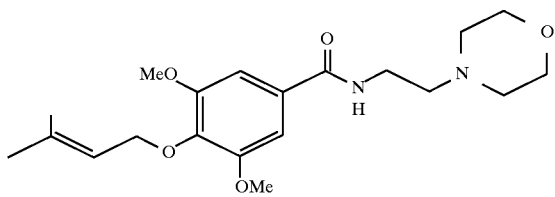

Example 42:

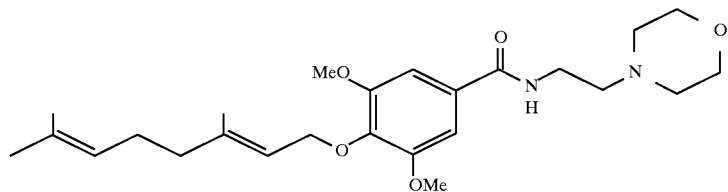

Example 43:

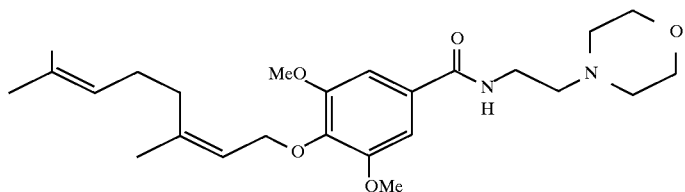

Example 44

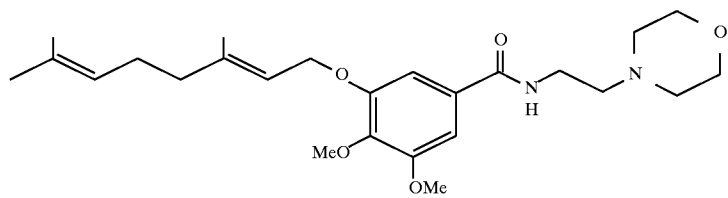

TABLE 6

| Example No. | Anti-ulcer Tests | | Tests for Safety | | |
|---|---|---|---|---|---|
| | WIS | CAP | PD | AT | MTT |
| 40 | 70 | | | | |
| 41 | 39 | | | | |
| 42 | 69 | 102 | | 4 | 0 |
| 43 | 41 | | 5 | 4 | 10 |
| 44 | 61 | 100 | | 4 | 22 |

As clearly from Table 6, even when $R_1$ and/or $R_2$ is an alkoxy group, a sufficient anti-ulcer effect and acid secretion inhibition effect can be obtained.

Compound Group 3

An alkylenediamine derivative of this compound group 3 has a basic structure expressed by formula 7 mentioned above, and wherein $R_1$ and $R_2$ are hydrogen atoms. As the alkylenediamine derivatives corresponding to this compound group 3, the following compounds were tested.

Example 45:
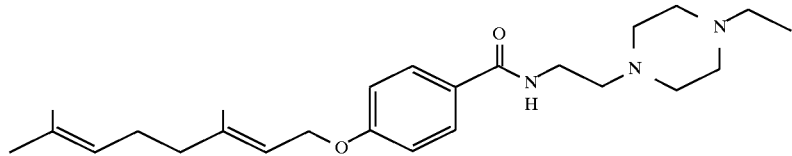
Example 46:
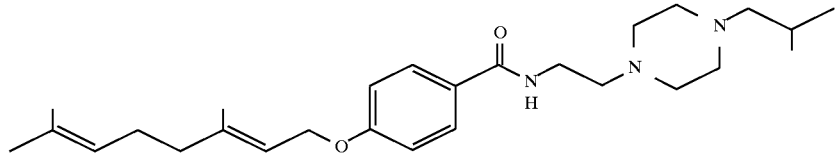
Example 47:
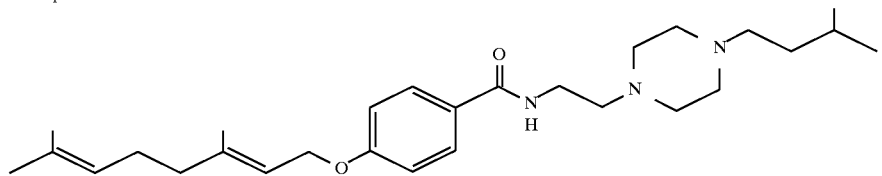
Example 48:
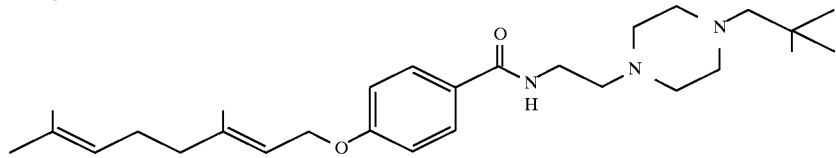
Example 49:
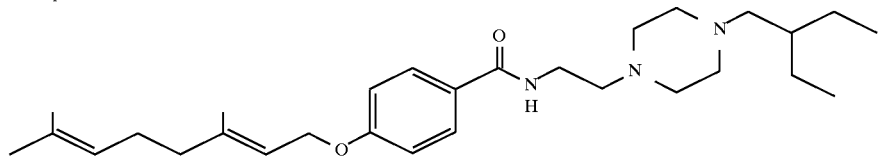
Example 50:
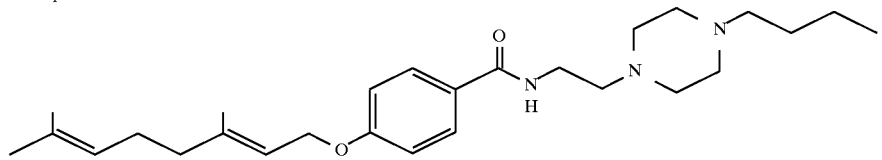
Example 51:
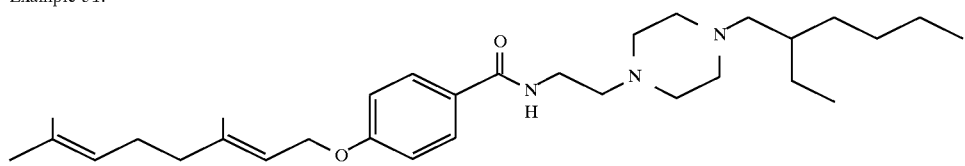
Example 52:
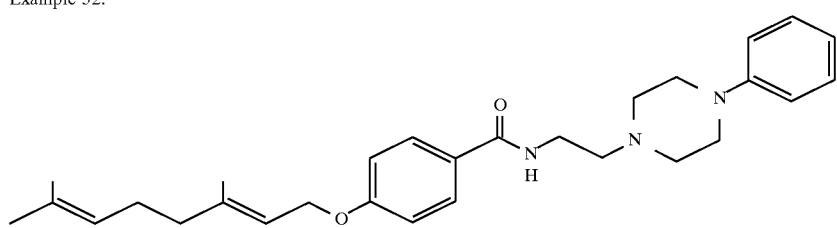

Example 53:
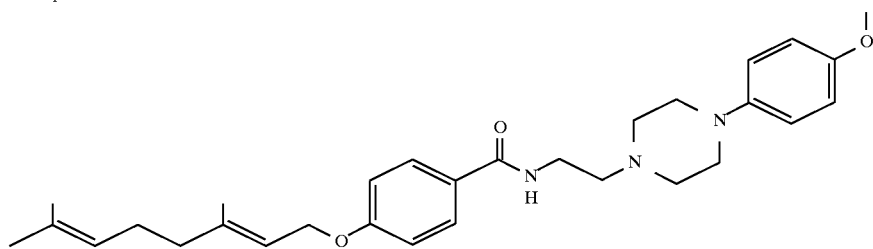
Example 54:
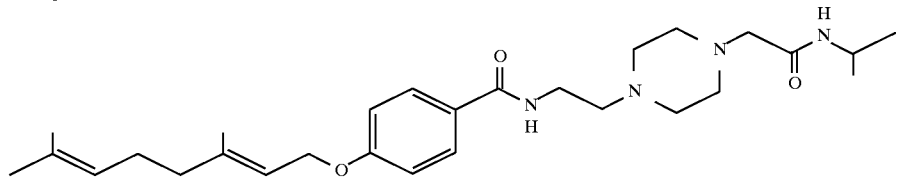
Example 55:
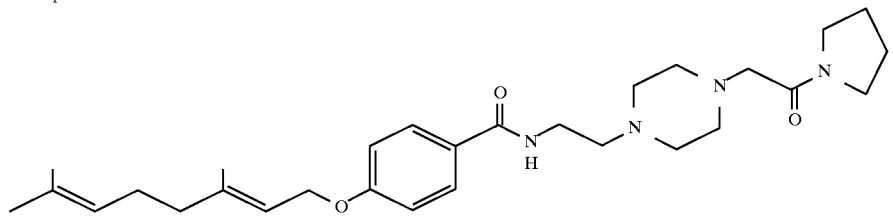
Example 56:
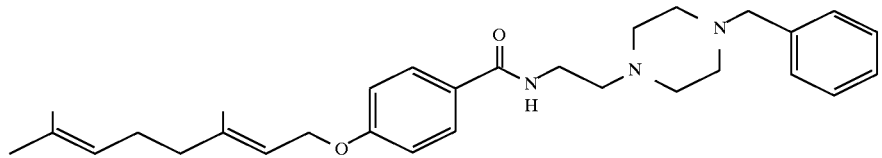
Example 57:
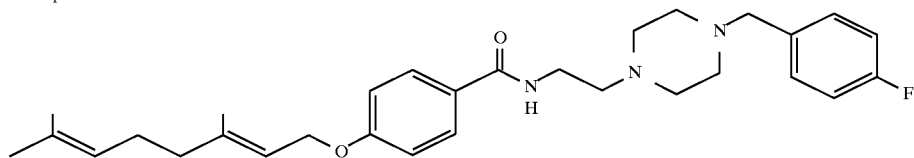
Example 58:
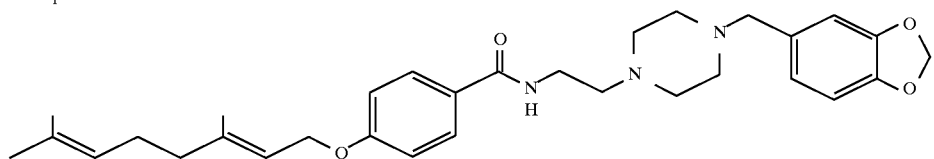
Example 59:
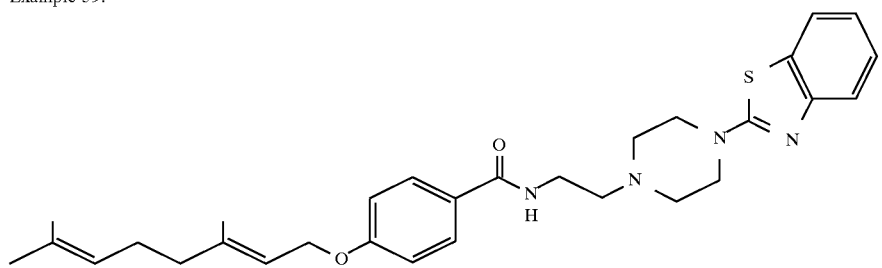

Example 60:

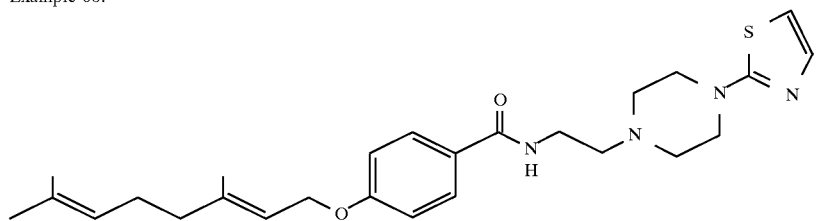

Example 61:

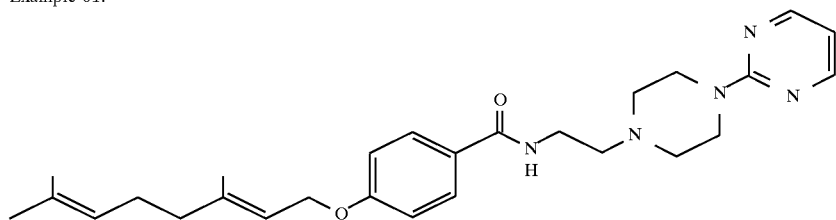

As clearly from results in Table 7, in this compound group 3, an anti-ulcer effect and acid secretion inhibition effect can be obtained. Further, as Example 59, there is a compound having an antibacterial activity against *Helicobacter pyroli* together with.

Here, in this compound group, $R_7$ can be selected with a high degree of freedom, whereby $R_7$ may be a lower alkyl group, an aryl group, a carbamoyl lower alkyl group, an aralkyl group, or an unsaturated heterocyclic group.

Compound Group 4

An alkylenediamine derivative in accordance with this compound group 4 has a basic structure expressed by formula 8 mentioned above. As the alkylenediamine derivative corresponding to the compound group 4, the following Example was tested.

Example 62:

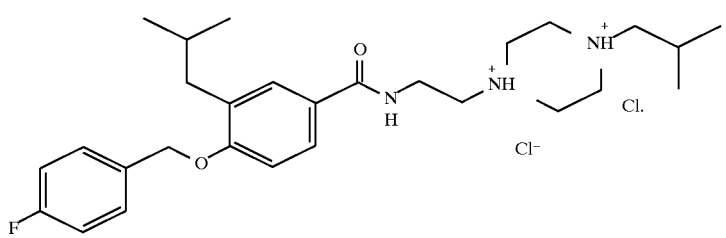

TABLE 7

| Example No. | Anti-ulcer Tests | | | | Anti-HP Test | Test for Safety |
|---|---|---|---|---|---|---|
| | WIS | VOL | TAO | CAP | AHP | MTT |
| 45 | 36 | | | 99 | | 30 |
| 46 | 78 | 33 | 34 | 100 | | 68 |
| 47 | | | | 101.2 | | |
| 48 | | | | 100.1 | | |
| 49 | | | | 99.8 | | |
| 50 | | | | 95.9 | | |
| 51 | | | | 94.8 | | |
| 52 | | | | 99.1 | | 11 |
| 53 | | | | 98.7 | | 7 |
| 54 | | | | 100.0 | | |
| 55 | | | | 99.2 | | 27 |
| 56 | | | | 99.4 | | |
| 57 | | | | 99.4 | | |
| 58 | 48 | | | 100.0 | | |
| 59 | 47 | | | 93.0 | 3.13> | 7 |
| 60 | | | | 100.1 | | 7 |
| 61 | | | | 100.1 | | 3 |

TABLE 8

| Example No. | Anti-ulcer Tests | | Anti-HP Test | Test for Safety |
|---|---|---|---|---|
| | WIS | CAP | AHP | AT |
| 62 | 77 | 102.5 | 3.13> | 3 |

As can be seen from the foregoing Table 8, the compound of this compound group 4 has an anti-ulcer effect and acid secretion inhibition effect as well as an antibacterial activity against *Helicobacter pyroli*.

In the following, the manufacturing method of Examples mentioned above will be explained.

At first, the synthetic methods of the material compounds used for synthesizing Examples of the present invention will be shown as Reference Examples 1 to 32.

Reference Example 1

Synthesis of 4-geranyloxybenzoic acid

To a solution of methyl 4-hydroxybenzoate (7.61 g) in acetone(80 ml) were added geranyl bromide (10.9 g) and potassium carbonate (13.8 g), and then the mixture was refluxed with heating for 6 hours. After the reaction, water (150 ml) was added to the reaction mixture, and the mixture was extracted with chloroform. The organic layer was dried over sodium sulfate anhydride and then concentrated under a vacuum. The residue was purified by silica gel column chromatography (hexane: ethyl acetate=9:1), thereby yielding 13.00 g of methyl 4-geranyloxybenzoate.

To a solution of methyl 4-geranyloxybenzoate(13.00 g) in methanol(50 ml) was added aqueous solution(10 ml) of potassium hydroxide (3.90 g). After being stirred overnight at room temperature, the mixture was refluxed with heating for 1 hour. After being acidified with concentrated hydrochloric acid, the reaction mixture was extracted with chloroform. The organic layer was dried over sodium sulfate anhydride and then the solvent was evaporated out under a vacuum. The resulting solid was recrystallized from hexane/ethyl acetate mixed solution, thereby yielding 9.77 g(71%) of the aimed compound.

Reference Example 2
Synthesis of 4-prenyloxybenzoic acid

In a manner identical to Reference Example 1, from methyl 4-hydroxy benzoate (7.61 g) and prenylbromide (7.45 g), 5.86 g (57%) of 4-prenyloxybenzoic acid was obtained.

Reference Example 3
Synthesis of 3-geranyloxybenzoic acid

In a manner identical to Reference Example 1, from methyl 3-hydroxy benzoate(7.61 g) and geranylbromide (10.86 g), 8.45 g(62%) of 3-geranyloxybenzoic acid was obtained.

Reference Example 4
Synthesis of 2-geranyloxybenzoic acid

In a manner identical to Reference Example 1, from methyl 2-hydroxy benzoate(7.61 g) and geranylbromide (10.86 g), 10.23 g(75%) of 2-geranyloxybenzoic acid was obtained.

Reference Example 5
Synthesis of 4-farnesyloxybenzoic acid

In a manner identical to Reference Example 1, from methyl 4-hydroxy benzoate(5.33 g) and farnesylbromide (10.00 g), 7.58 g(63%) of 4-farnesyloxybenzoic acid was obtained.

Reference Example 6
Synthesis of 2-geranylthiobenzoic acid

In a manner identical to Reference Example 1, from methyl 4-mercapto benzoate(8.36) and geranylbromide (10.86 g), 10.97 g(76%) of 2-geranylthiobenzoic acid was obtained.

Reference Example 7
Synthesis of 2-geranyloxy-5-methoxybenzoic acid

To a solution of 2-hydroxy-5-methoxybenzoic acid (8.40 g) in ethanol (100 ml) was added sulfuric acid (5 ml) and then the mixture was refluxed with heating for 3 hours. After the reaction, the reaction mixture was concentrated and then water(100 ml) and sodium hydrogencarbonate were added thereto. The mixture was extracted with chloroform and the extract was purified by silica gel column chromatography (hexane: ethyl acetate), thereby yielding ethyl 2-hydroxy-5-methoxybenzoate.

In a manner identical to Reference Example 1, from the resulting compound (9.10 g) and geranylbromide(10.86 g), 7.34 g(48%) of 2-geranyloxy-5-methoxybenzoic acid was obtained.

Reference Example 8
Synthesis of 3,4-diprenyloxybenzoic acid

In a manner identical to Reference Example 1, from ethyl 3,4-dihydroxy benzoate(9.10 g) and prenylbromide(14.90 g), 11.61 g(67%) of 3,4-diprenyloxybenzoic acid was obtained.

Reference Example 9
Synthesis of 3,4-digeranyloxybenzoic acid

In a manner identical to Reference Example 1, from ethyl 3,4-dihydroxy benzoate(9.10 g) and geranylbromide(21.70 g), 13.1 g(62%) of 3,4-digeranyloxybenzoic acid was obtained.

Reference Example 10
Synthesis of 2,4-digeranyloxybenzoic acid

In a manner identical to Reference Example 7, from 2,4-dihydroxybenzoic acid(9.10 g) and geranylbromide (21.70 g), 8.34 g(52%) of 2,4-digeranyloxybenzoic acid was obtained.

Reference Example 11
Synthesis of 4,5-dimethoxy-3-geranyloxybenzoic acid

In a manner identical to Reference Example 1, from methyl 4,5-dimethoxy-3-hydroxybenzoate(7.00 g) and geranylbromide(10.30 g), 5.62 g(51%) of 4,5-dimethoxy-3-geranyloxybenzoic acid was obtained.

Reference Example 12
Synthesis of methyl 3,5-dimethoxy-4-hydroxybenzoate

In a manner identical to Reference Example 7, from syringic acid (17.03 g) and methanol, 13.85 g(76%) of methyl 3,5-dimethoxy-4-hydroxybenzoate was obtained.

Reference Example 13
Synthesis of 3,5-dimethoxy-4-prenyloxybenzoic acid

In a manner identical to Reference Example 1, from methyl 3,5-dimethoxy-4-hydroxybenzoate(7.89 g) and prenylchloride(5.73 g), 5.40 g(55%) of 3,5-dimethoxy-4-prenyloxybenzoic acid was obtained.

Reference Example 14
Synthesis of 3,5-dimethoxy-4-geranyloxybenzoic acid

In a manner identical to Reference Example 1, from methyl 3,5-dimethoxy-4-hydroxybenzoate(5.44 g) and geranylbromide(8.04 g), 5.71 g(67%) of 3,5-dimethoxy-4-geranyloxybenzoic acid was obtained.

Reference Example 15
Synthesis of 4-neryloxybenzoic acid

To a solution of neryl(7.71 g) in dichloromethane(200 ml) were added N-chlorosuccinimide(10.01 g) and dimethylsulfide(6.56 ml) and then the mixture was stirred while being cooled with ice for 4 hours. After the reaction, the reaction mixture was washed with saturated brine and water successively, dried over sodium sulfate anhydride, and concentrated.

In a manner identical to Reference Example 1, from nerylchloride obtained and methyl 4-hydroxybenzoate(7.61 g), 7.47 g(54%) of 4-neryloxybenzoic acid was obtained.

Reference Example 16
Synthesis of 3,5-dimethoxy-4-neryloxybenzoic acid

In a manner identical to Reference Example 15, from nerol(1.26 g) and methyl 3,5-dimethoxy-4-hydroxybenzoate (0.96 g), 0.19 g(9%) of 3,5-dimethoxy-4-neryloxybenzoic acid was obtained.

Reference Example 17
Synthesis of 3,4,5-triprenyloxybenzoic acid

In a manner identical to Reference Example 1, from ethyl 3,4,5-trihydroxy benzoate(4.95 g) and prenylbromide(14.90 g), 5.43 g(58%) of 3,4,5-triprenyloxybenzoic acid was obtained.

Reference Example 18
Synthesis of 2-geranyloxy-4-methoxybenzoic acid
In a manner identical to Reference Example 1, from methyl 2-hydroxy-4-methoxybenzoate(9.1 g) and geranylbromide(10.86 g), 7.73 g(51%) of 2-geranyloxy-4-methoxybenzoic acid was obtained.

Reference Example 19
Synthesis of 4-geranyloxy-3-methoxybenzoic acid
In a manner identical to Reference Example 1, from methyl 4-hydroxy-3-methoxybenzoate(9.1 g) and geranylbromide(10.86 g), 7.59 g(63%) of 4-geranyloxy-3-methoxybenzoic acid was obtained.

Reference Example 20
Synthesis of 3-geranyloxy-4-methoxybenzoic acid
In a manner identical to Reference Example 7, from 2-hydroxy-3-methoxybenzoic acid (16.80 g) and geranylbromide (10.86 g), 11.54 g (64%) of 2-geranyloxy-3-methoxybenzoic acid was obtained.

Reference Example 21
Synthesis of 3-geranyloxy-4-methoxybenzoic acid
In a manner identical to Reference Example 1, from methyl 3-hydroxy-4-methoxybenzoate(8.40 g) and geranylbromide(10.36 g), 3.60 g(24%) of 3-geranyloxy-4-methoxybenzoic acid was obtained.

Reference Example 22
Synthesis of 3,5-diprenyloxybenzoic acid
In a manner identical to Reference Example 1, from methyl 3,5-dihydroxy benzoate(8.40 g) and prenylbromide (14.90 g), 10.06 g(69%) of 3,5-diprenyloxybenzoic acid was obtained.

Reference Example 23
Synthesis of 2,4-diprenyloxybenzoic acid
In a manner identical to Reference Example 1, from methyl 2,4-dihydroxy benzoate(8.40 g) and prenylbromide (14.90 g), 8.86 g(61%) of 2,4-diprenyloxybenzoic acid was obtained.

Reference Example 24
Synthesis of 2,5-diprenyloxybenzoic acid
In a manner identical to Reference Example 7, from methyl 2,5-dihydroxy benzoic acid (23.10 g) and prenylbromide (14.90 g), 9.74 g (84%) of 2,5-diprenyloxy benzoic acid was obtained.

Reference Example 25
Synthesis of 3,5-digeranyloxybenzoic acid
In a manner identical to Reference Example 1, from methyl 3,5-dihydroxy benzoate(8.40 g) and geranylbromide (21.72 g), 10.09 g(47%) of 3,5-digeranyloxybenzoic acid was obtained.

Reference Example 26
Synthesis of 2,5-digeranyloxybenzoic acid
In a manner identical to Reference Example 1, from methyl 2,5-dihydroxy benzoate(7.12 g) and geranylbromide (21.72 g), 2.17 g(10%) of 2,5-digeranyloxybenzoic acid was obtained.

Reference Example 27
Synthesis of 3-fluoro-6-geranyloxybenzoic acid

In a manner identical to Reference Example 7, from 3-fluoro-6-hydroxybenzoic acid(10.00 g) and geranylbromide(10.86 g), 11.57 g(79%) of 3-fluoro-6-geranyloxybenzoic acid was obtained.

Reference Example 28
Synthesis of 4-(2-aminoethyl)-1-ethylpiperazine
To a solution of 1-piperazineethanol(2.28 g) in acetone(40 ml) were added bromoacetonitrile(2.40 g) and potassium carbonate(5.53 g) and then the mixture was stirred at room temperature for 4 hours. After the reaction, the reaction mixture was washed with saturated brine and water successively, dried over sodium sulfate anhydride, and concentrated under a vacuum. To the residue dissolved in methanol(60 ml) were added cobalt chloride(9.50 g) and sodium borohydride(7.60 g), and then the mixture was stirred at room temperature for 30 minutes. After the reaction mixture was concentrated, the resulting residue was dissolved in chloroform. After a filtration, the filtrate was concentrated, thereby yielding 1.17 g (41%) of 4-(2-aminoethyl)-1-ethylpiperazine.

Reference Example 29
Synthesis of 4-(2-aminoethyl)-1-isobutylpiperazine
1-piperazinecarboxaldehyde(33.21 g) and potassium carbonate(68.34 g) were dissolved in acetone(150 ml) and then isobutylbromide(47.43 g) was added thereto. After being refluxed with stirring for 24 hours, the reaction mixture was filtrated. The filtrate was concentrated under a vacuum and the resulting residue was dissolved in ethyl acetate. The solution was washed with water and saturated brine successively, dried over sodium sulfate anhydride, and concentrated under a vacuum, thereby yielding 36.85 g of residue. A solution of the residue (27.8 g) in methanol (160 ml), with 2N hydrochloric acid methanol solution (180 ml) added thereto, was stood at room temperature for 60 hours. The reaction mixture was concentrated under a vacuum and acetone was added to the resulting residue. The crystals deposited were collected by filtration, washed with acetone, and dried, thereby yielding 34.8 g of 1-isobutylpiperazine dihydrochloride.

To 1-isobutylpiperazine dihydrochloride(69.5 g) was added 10% aqueous solution of sodium hydrochloride(100 ml) and the mixture was extracted with ether. After being concentrated, the extract was distilled under a vacuum(bp 172°–174° C./5 mmHg), thereby yielding 43.7 g of 1-isobutylpiperazine.

By using 1-isobutylpiperazine (2.84 g) and bromoacetonitrile(2.40 g), as in the case of Reference Example 28, 1.19 g (15%) of 4-(2-aminoethyl)-1-isobutylpiperazine was obtained.

Reference Example 30
Synthesis of 1-(2-aminoethyl)-2,6-dimethylmorphorine
In a manner identical to Reference Example 28, from 2,6-dimethyl morphorine(3.46 g) and chloroacetonitrile (2.27 g), 2.97 g(63%) of 1-(2-aminoethyl)-2,6-dimethylmorphorine was obtained.

Reference Example 31
Synthesis of 1-[2-(ethylamino)ethyl]piperidine
To a solution of 1-(2-aminoethyl)piperidine(5.01 g) in dichloromethane (100 ml) were added triethylamine(11 ml) and acetic anhydride(4.4 ml) and then the mixture was stirred at room temperature for 40 minutes. The reaction solution was washed with saturated sodium hydrogencarbonate aqueous solution and saturated brine successively, dried over sodium sulfate anhydride, and concentrated under a vacuum. The residue was dropped into a suspension of lithium aluminium hydride (3.46 g) in tetrahydrofuran(100 ml). After being refluxed with heating for 1 hour, the reaction mixture was filtrated. The filtrate was concentrated, thereby yielding 4.43 g(79%) of 1-[2-(ethylamino)ethyl] piperidine.

Reference Example 32

Synthesis of 1-(2-aminoethyl)-3,3-dimethylpiperidine

In a manner identical to Reference Example 28, from 3,3-dimethyl piperidine(3.40 g) and chloroacetonitrile(2.27 g), 2.32 g(50%) of 1-(2-aminoethyl)-3,3-dimethylpiperidine was obtained.

In the following, the synthesizing method of Examples 1 to 62 mentioned above which are compounds in accordance with the present invention will be shown.

Example 1

In a manner identical to Example 45, 4-prenyloxybenzoic acid(1.44 g) was subjected to a condensation reaction with 1-(2-aminoethyl)piperidine(1.08 ml), thereby yielding 1.77 g(80%) of the aimed compound.

m.p. 86.2°–87.0° C. $^1$H-NMR (CDCl$_3$) δ (ppm) 7.74(2H, d,J=8.8 Hz), 6.93(2H,d,J=8.8 Hz), 6.85(1H,bs), 5.49(1H,t, j=6.6 Hz), 4.55(2H,d,J=6.8 Hz), 3.51(2H,q,J=5.9 Hz), 2.54 (2H,t,J=6.1 Hz), 2.51–2.39(4H,m), 180 (3H,s), 1.75(3H,s), 1.61–1.58(4H,m), 1.50–1.42(2H,m).

Example 2

In a manner identical to Example 45, 4-neryloxybenzoic acid(1.64 g) was subjected to a condensation reaction with 1-(2-aminoethyl)piperidine(0.84 ml), thereby yielding 1.09 g(47%) of the aimed compound.

m.p. 59.8°–61.2 ° C. $^1$H-NMR (CDCl$_3$) δ (ppm) 7.73(2H, d,J=8.8 Hz), 6.93(2H,d,J=8.8 Hz), 6.85(1H,bs), 5.50(1H,t, j=6.8 Hz), 5.12(1H,t,J=5.8 Hz), 4.54(2H,d,J=6.8 Hz), 3.51 (2H,q,J=5.8 Hz), 2.54(2H,t,J=5.8 Hz), 2.38–2.48(4H,m), 2.17–2.07(4H,m), 1.80(3H,s), 1.68(3H,s), 1.62–1.57(7H,m), 1.52–1.42(2H,m).

Example 3

In a manner identical to Example 45, 4-geranyloxybenzoic acid(1.37 g) was subjected to a condensation reaction with 1-(2-aminoethyl)piperidine(0.70 ml), thereby yielding 1.70 g(88%) of the aimed compound.

m.p. 62.2–63.5° C. $^1$H-NMR (CDCl$_3$) δ (ppm) 7.73(2H, dd,J=1.5 Hz,8.3 Hz), 6.92(2H,dd,J=2.0 Hz,8.8 Hz), 6.88 (1H,bs), 5.48 (1H,t,J=6.3 Hz), 5.13–5.06(1H,m), 4.57(2H, d,J=6.4 Hz), 3.51(2H,q,J=5.4 Hz), 2.55(2H,t,J=5.9 Hz), 2.51–2.39(4H,m), 2.18–2.02(4H,m), 1.74(3H,s), 1.67(3H,s), 1.60(3H,s), 1.50–1.42(2H,m).

Example 4

In a manner identical to Example 45, 3-geranyloxybenzoic acid(1.37 g) was subjected to a condensation reaction with 1-(2-aminoethyl)piperidine(0.70 ml), thereby yielding 1.75 g(91%) of the aimed compound.

$^1$H-NMR (CDCl$_3$) δ (ppm) 7.41–7.23(3H,m), 7.03(2H,dt, J=2.4 Hz,7.3 Hz), 6.99(1H,bs), 5.49(1H,t,J=6.4 Hz), 5.13–5.05(1H,m), 4.58(2H,d,J=6.4 Hz), 3.53(2H,q,J=5.4 Hz), 2.56(2H,t,J=6.1 Hz), 2.52–2.38(4H,m), 2.17–2.03(4H, m), 1.74(3H,s), 1.68(3H,s), 1.60(3H,s), 1.51–1.39(2H,m).

Example 5

In a manner identical to Example 45, 2-geranyloxybenzoic acid(1.37 g) was subjected to a condensation reaction with 1-(2-aminoethyl)piperidine(0.70 ml), thereby yielding 1.70 g(89%) of the aimed compound.

$^1$H-NMR (CDCl$_3$) δ (ppm) 8.34(1H,bs), 8.21(1H,dd,J= 2.0 Hz,7.8 Hz), 7.40(1H,dt,J=2.0 Hz,8.3 Hz), 7.05 (1H,t,J= 7.8 Hz), 6.94(1H,d,J=8.3 Hz), 5.50(1H,t,J=6.4 Hz), 5.11–5.02(1H,m), 4.72(2H,d,J=6.4 Hz), 3.56(2H,q,J=6.4 Hz), 2.53(2H,t,J=6.4 Hz), 2.49–2.34(4H,m), 2.16–2.02 (4H, m), 1.75(3H,s), 1.66(3H,s), 1.60(3H,s), 1.49–1.39(2H,m).

Example 6

In a manner identical to Example 45, 5-fluoro-2-geranyloxybenzoic acid (1.46 g) was subjected to a condensation reaction with 1-(2-aminoethyl)piperidine (0.70 ml), thereby yielding 1.06 g(53%) of the aimed compound.

$^1$H-NMR (CDCl$_3$) δ (ppm) 8.40(1H,bs), 7.94–7.89(1H, m), 7.10–7.03(1H,m), 6.93–6.87(1H,m), 5.52–5.42(1H,m), 5.10–5.00(1H,m), 4.70(2H,d,J=6.4 Hz), 3.60–3.48(2H,m), 2.57–2.37 (6H,m), 2.15–2.05(4H,m), 1.74(3H,s), 1.66(3H, s), 1.60–1.44(9H,m).

Example 7

In a manner identical to Example 45, 2-geranylthiobenzoic acid(2.03 g) was subjected to a condensation reaction with 1-(2-aminoethyl)piperidine (1.00 ml), thereby yielding 0.86 g(31%) of the aimed compound.

$^1$H-NMR (CDCl$_3$) δ (ppm) 7.66(1H,d,J=8.8 Hz), 7.42–7.23(3H,m), 5.28(1H,t,J=7.8 Hz), 5.04(1H,t,J=6.8 Hz), 3.57–3.54(4H,m), 2.54(2H,t,J=6.4 Hz), 2.46–2.39(4H, m), 2.08–1.95(4H,m), 1.67(3H,s), 1.66(3H,s), 1.58(3H,s), 1.47–1.43(2H,m).

Example 8

In a manner identical to Example 45, 4-geranyloxybenzoic acid(1.91 g) was subjected to a condensation reaction with 1-[2-(ethylamino)ethyl]piperidine (1.20 g), thereby yielding 2.13 g(74%) of the aimed compound.

$^1$H-NMR (CDCl$_3$) δ (ppm) 7.73(2H,dd,J=1.5 Hz,8.3 Hz), 6.92(2H,dd,J=2.0 Hz,8.8 Hz), 5.48(1H,t,J=6.4 Hz), 5.13–5.06(1H,m), 4.57(2H,d,J=6.4 Hz), 3.75–3.20(4H,m), 2.72–2.20(6H,m), 2.18–2.02 (4H,m), 1.74(3H,s), 1.67(3H, s), 1.60(3H,s), 1.55(3H,s), 1.46(2H,s), 1.10–1.28(4H,m).

Example 9

In a manner identical to Example 45, 4-geranyloxybenzoic acid(1.92 g) was subjected to a condensation reaction with 1-(2-aminoethyl)-3,3-dimethylpiperidine (1.00 g), thereby yielding 1.63 g(56%) of the aimed compound.

$^1$H-NMR (CDCl$_3$) δ (ppm) 7.73(2H,d,J=8.8 Hz), 6.92 (2H,d,J=8.8 Hz), 5.48(1H,t,J=6.6 Hz), 5.09(1H,t,J=6.6 Hz), 4.58(2H,d,J=6.3 Hz), 3.50(2H,q,J=5.4 Hz), 2.51(2H,t,J=5.9 Hz), 2.12–2.10 (6H,m), 1.74(3H,s), 1.68(3H,s), 1.62–1.60 (5H,m), 1.26(2H,t,J=6.8 Hz), 0.97(6H,s).

Example 10

In a manner identical to Example 45, 4-farnesyloxybenzoic acid(1.71 g) was subjected to a condensation reaction with 1-(2-aminoethyl)piperidine(0.70 ml), thereby yielding 2.23 g(99%) of the aimed compound.

m.p. 86.2°–87.0° C. $^1$H-NMR (CDCl$_3$) δ (ppm) 7.74(2H, d,J=8.3 Hz), 6.93(2H,d,J=8.8 Hz), 6.88(1H,bs), 5.49(1H,t, J=6.6 Hz), 5.07–5.11(2H,m), 4.57(2H,d,J=6.8 Hz), 3.51(2H, q,J=5.4 Hz), 2.55(2H,t,J=6.1 Hz), 2.51–2.39(4H,m), 2.15–2.03(6H,m), 1.75(3H,s), 1.68(3H,s), 1.60–1.57(12H, m).

Example 11

In a manner identical to Example 45, 3,4-digeranyloxybenzoic acid(2.13 g) was subjected to a condensation reaction with 1-(2-aminoethyl)piperidine(0.70 ml), thereby yielding 2.17 g(81%) of the aimed compound.

m.p. 99.5°–100.8° C. $^1$H-NMR (CDCl$_3$) δ (ppm) 7.43 (1H,d,J=2.0 Hz), 7.28–7.23(1H,m), 6.87(1H,d,J=8.3 Hz), 5.56–5.45 (2H,m), 5.12–5.03(2H,m), 4.66(4H,d,J=6.4 Hz), 3.54–3.46(2H,m), 2.56–2.48(2H,m), 2.47–2.34(4H,m), 2.15–2.00(8H,m), 1.74(3H,s), 1.72(3H,s), 1.66(6H,s), 1.59 (6H,s), 1.51–1.39(2H,m).

Example 12

In a manner identical to Example 45, 2,4-digeranyloxybenzoic acid(2.13 g) was subjected to a condensation reaction with 1-(2-aminoethyl)piperidine(0.70 ml), thereby yielding 2.10 g(79%) of the aimed compound.

$^1$H-NMR (CDCl$_3$) δ (ppm) 8.20(1H,bs), 8.15(1H,d,J=8.8 Hz), 6.58(1H,dd,J=2.0 Hz,6.8 Hz), 6.49(1H,d,J=2.0 Hz), 5.52–5.46(2H,m), 5.09–5.07(2H,m), 4.67(2H,d,J=6.4 Hz), 4.56(2H,d,J=6.4 Hz), 3.54(2H,d,J=4.9 Hz), 2.59–2.45(2H,m), 2.42(4H,bs), 2.15–2.05(8H,m), 1.74 (6H,s), 1.68–1.67 (6H,m), 1.60–1.59(2H,m).

Example 13

In a manner identical to Example 45, 2,5-digeranyloxybenzoic acid(2.13 g) was subjected to a condensation reaction with 1-(2-aminoethyl)piperidine(0.70 ml), thereby yielding 2.06 g(77%) of the aimed compound.

$^1$H-NMR (CDCl$_3$) δ (ppm) 8.43(1H,bs), 7.79(1H,d,J=3.4 Hz), 6.99(1H,dd,J=3.4 Hz,8.8 Hz), 6.90(1H,d,J=8.8 Hz), 5.53–5.42(2H,m), 5.11–5.02(2H,m), 4.63(2H,d,J=6.4 Hz), 4.52(2H,d,J=6.4 Hz), 3.52(2H,q,J=6.4 Hz), 2.55(2H,t,J=6.4 Hz), 2.50–2.37(4H,m), 2.17–2.02 (8H,m), 1.72(6H,s), 1.67 (6H,s), 1.60(6H,s), 1.51–1.39(2H,m).

Example 14

In a manner identical to Example 45, 3,5-digeranyloxybenzoic acid(2.13 g) was subjected to a condensation reaction with 1-(2-aminoethyl)piperidine(0.70 ml), thereby yielding 2.24 g(84%) of the aimed compound.

$^1$H-NMR (CDCl$_3$) δ (ppm) 6.94(2H,d,J=2.4 Hz), 6.61 (1H,t,J=2.4 Hz), 5.49(2H,t,J=5.4 Hz), 5.12–5.04 (2H,m), 4.51(4H,d,J=6.8 Hz), 3.52(2H,q,J=5.9 Hz), 2.56(2H,t,J=5.8 Hz), 2.51–2.37 (4H,m), 2.17–2.04(8H,m), 1.73(6H,s), 1.68 (6H,s), 1.60(6H,s), 1.50–1.41(2H,m).

Example 15

In a manner identical to Example 45, 3,4-diprenyloxybenzoic acid(1.45 g) was subjected to a condensation reaction with 1-(2-aminoethyl)piperidine(0.70 ml), thereby yielding 1.80 g(90%) of the aimed compound.

m.p. 101.5°–102.5° C. $^1$H-NMR (CDCl$_3$) δ (ppm) 7.43 (1H,d,J=2.0 Hz), 6.85(1H,d,J=8.3 Hz), 5.55–5.46(2H,m), 4.62(4H,d,J=4.4 Hz), 3.56–3.48(2H,m), 2.58–2.52(2H,m), 2.51–2.40(4H,m), 1.77(6H,s), 1.74 (3H,s), 1.73(3H,s), 1.64–1.51(4H,m), 1.51–1.43(2H,m).

Example 16

In a manner identical to Example 45, 2,4-diprenyloxybenzoic acid(1.45 g) was subjected to a condensation reaction with 1-(2-aminoethyl)piperidine(0.70 ml), thereby yielding 1.88 g(94%) of the aimed compound.

$^1$H-NMR (CDCl$_3$) δ (ppm) 8.19–8.15(2H,m), 6.59(1H,d, J=2.4 Hz), 6.49(1H,d,J=2.2 Hz), 5.52–5.48 (2H,m), 4.63 (2H,d,J=5.9 Hz), 4.54(2H,d,J=6.3 Hz), 3.56–3.53(2H,m), 2.52(2H,t,J=6.4 Hz), 2.42(4H,s), 1.80(6H,s), 1.75(6H,s), 1.58–1.57(4H,m), 1.49–1.40(2H,m).

Example 17

In a manner identical to Example 45, 2,5-diprenyloxybenzoic acid(1.45 g) was subjected to a condensation reaction with 1-(2-aminoethyl)piperidine(0.70 ml), thereby yielding 1.68 g(84%) of the aimed compound.

m.p. 46.0°–47.8° C. $^1$H-NMR (CDCl$_3$) δ (ppm) 8.43(1H, bs), 7.79(1H,d,J=3.4 Hz), 6.99(1H,dd,J=3.4 Hz,8.8 Hz), 6.90(1H,d,J=8.8 Hz), 5.51–4.95(2H,m), 4.63(2H,d,J=6.4 Hz), 4.52(2H,d,J=6.4 Hz), 3.52(2H,q,J=6.4 Hz), 2.55(2H,t, J=6.4 Hz), 2.50–2.37(4H,m), 1.80(6H,s), 1.74(6H,s), 1.51–1.39(2H,m).

Example 18

In a manner identical to Example 45, 3,5-diprenyloxybenzoic acid(2.03 g) was subjected to a condensation reaction with 1-(2-aminoethyl)piperidine(1.00 ml), thereby yielding 2.22 g(79%) of the aimed compound.

$^1$H-NMR (CDCl$_3$) δ (ppm) 6.94(2H,d,J=2.4 Hz), 6.61 (1H,t,J=2.4 Hz), 5.49(2H,t,J=5.4 Hz), 4.51(4H,d,J=6.8 Hz), 3.52(2H,q,J=5.9 Hz), 2.56(2H,t,J=5.8 Hz), 2.51–2.37(4H, m), 1.80(6H,s), 1.74(6H,s), 1.64–1.55(4H,m), 1.50–1.41 (2H,m).

Example 19

In a manner identical to Example 45, 3,4,5-triprenyloxybenzoic acid(13.11 g) was subjected to a condensation reaction with 1-(2-aminoethyl)piperidine(5.42 ml), thereby yielding 11.98 g(71%) of the aimed compound.

m.p. 75.0–79.5° C. $^1$H-NMR (CDCl$_3$) δ (ppm) 7.02(2H, s), 6.84(1H,s), 5.56–5.42(3H,m), 4.62–4.50(6H,m), 3.53–3.40 (2H,m), 2.57–2.47(2H,m), 2.46–2.34(4H,m), 1.78–1.52(22H,m), 1.50–1.37(2H,m).

Example 20

In a manner identical to Example 45, 2-geranyloxy-5-methoxybenzoic acid(1.52 g) was subjected to a condensation reaction with 1-(2-aminoethyl)piperidine (0.70 ml), thereby yielding 1.70 g(82%) of the aimed compound.

$^1$H-NMR (CDCl$_3$) δ (ppm) 8.45(1H,bs), 7.76(1H,d,J=3.0 Hz), 7.06–6.82(2H,m), 5.77–5.50(1H,m), 5.10–4.94(1H,m), 4.67(2H,d,J=6.8 Hz), 3.81(3H,s), 3.61–3.46(2H,m), 2.06–2.30(6H,m), 2.13–2.00(4H,m), 1.72(3H,s), 1.67(3H,s), 1.60(3H,s), 1.49–1.35(2H,m).

Example 21

In a manner identical to Example 45, 2-geranyloxy-3-methoxybenzoic acid(1.52 g) was subjected to a condensation reaction with 1-(2-aminoethyl)piperidine (0.70 ml), thereby yielding 1.49 g(72%) of the aimed compound.

$^1$H-NMR (CDCl$_3$) δ (ppm) 8.38(1H,bs), 7.70(1H,dd,J= 2.0 Hz,7.8 Hz), 7.12(1H,dt,J=2.0 Hz,7.8 Hz), 7.00 (1H,d,J= 8.3 Hz), 5.53(1H,t,J=7.3 Hz), 5.07–5.02(1H,m), 4.64(2H,d, J=7.3 Hz), 3.89 (3H,s), 3.56(2H,q,J=6.3 Hz), 2.53(2H,t,J= 6.3 Hz),2.49–2.33(4H,m), 2.12–1.97 (4H,m), 1.67(3H,s), 1.62(3H,s), 1.59(3H,s), 1.48–1.39(2H,m).

Example 22

In a manner identical to Example 45, 2-geranyloxy-4-methoxybenzoic acid(1.52 g) was subjected to a condensation reaction with 1-(2-aminoethyl)piperidine (0.70 ml), thereby yielding 1.39 g(67%) of the aimed compound.

¹H-NMR (CDCl₃) δ (ppm) 8.22(1H,bs), 8.17(1H,d,J=8.8 Hz), 6.57(1H,dd,J=2.0 Hz,8.8 Hz), 6.47(1H,d,J=2.0 Hz), 5.56–5.47(1H,m), 5.10–5.03(1H,m), 4.69(2H,d,J=6.4 Hz), 3.83(3H,s), 3.55 (2H,q,J=6.4 Hz), 2.52(2H,t,J=6.4 Hz), 2.48–2.35(4H,m), 2.17–2.04(4H,m), 1.76(3H,s), 1.66(3H,s), 1.60(3H,s), 1.50–1.36(2H,m).

Example 23

In a manner identical to Example 45, 3-geranyloxy-4-methoxybenzoic acid(1.54 g) was subjected to a condensation reaction with 1-(2-aminoethyl)piperidine (0.70 ml), thereby yielding 1.56 g(75%) of the aimed compound.

m.p. 101.0°–102.5° C. ¹H-NMR (CDCl₃) δ (ppm) 7.45 (1H,bs), 7.28(1H,d,J=8.3 Hz), 6.87(1H,d,J=8.3 Hz), 5.54 (1H,t,J=6.4 Hz), 5.09(1H,t,J=6.8 Hz), 4.66(2H,d,J=6.8 Hz), 3.90(3H,s), 3.51(2H,q,J=5.4 Hz), 2.55(2H,t,J=5.4 Hz), 2.51–2.36(4H,m), 2.16–2.04(4H,m), 1.75(3H,s), 1.66(3H,s), 1.60(3H,s), 1.52–1.41(2H,m).

Example 24

In a manner identical to Example 45, 4,5-dimethoxy-3-geranyloxybenzoic acid(1.34 g) was subjected to a condensation reaction with 1-(2-aminoethyl)piperidine (0.62 ml), thereby yielding 1.60 g(90%) of the aimed compound.

¹H-NMR (CDCl₃) δ (ppm) 7.25–7.07(2H,m), 5.52(1H,t, J=5.4 Hz), 5.08(1H,t,J=5.4 Hz), 4.64(2H,d,J=6.8 Hz), 3.90 (3H,s), 3.88(3H,s), 3.55–3.51(2H,m), 2.58(2H,t,J=5.9 Hz), 2.55–2.38 (4H,m), 2.13–2.05(4H,m), 1.74(3H,s), 1.67(3H, s), 1.60(3H,s), 1.65–1.42(6H,m).

Example 25

In a manner identical to Example 45, 4-geranyloxy-3-methoxybenzoic acid(1.52 g) was subjected to a condensation reaction with 1-(2-aminoethyl)piperidine (0.70 ml), thereby yielding 1.71 g(83%) of the aimed compound.

m.p. 82.2°–82.8° C. ¹H-NMR (CDCl₃) δ (ppm) 7.44(1H, d,J=2.0 Hz), 7.25(1H,dd,J=2.0 Hz,8.3 Hz), 6.86(1H,d,J=8.3 Hz), 6.91 (1H,bs), 5.50(1H,t,J=6.8 Hz), 5.08(1H,t,J=6.4 Hz), 4.66(2H,d,J=6.4 Hz), 3.91(3H,s), 3.52 (2H,q,J=6.4 Hz), 2.55(2H,t,J=6.4 Hz), 2.50–2.37(4H,m), 2.16–1.96(4H,m), 1.73(3H,s), 1.67(3H,s), 1.59(3H,s), 1.51–1.39(2H,m).

Example 26

In a manner identical to Example 45, 3,5-dimethoxy-4-geranyloxybenzoic acid(1.80 g) was subjected to a condensation reaction with 1-(2-aminoethyl)piperidine (0.69 g), thereby yielding 0.70 g(29%) of the aimed compound.

m.p. 70.0°–72.0° C. ¹H-NMR (CDCl₃) δ (ppm) 7.03(2H, s), 6.95(1H,s), 5.60–5.52(1H,m), 5.12–5.05(1H,m), 4.58 (2H,d,J=7.3 Hz), 3.90(6H,s), 3.57–3.50(2H,m), 2.65–2.55 (2H,m), 2.53–2.40(4H,m), 2.09–2.03(4H,m), 1.88–1.58 (13H,m), 1.52–1.42(2H,m).

Example 27

In a manner identical to Example 45, 3,5-dimethoxy-4-prenyloxybenzoic acid(1.86 g) was subjected to a condensation reaction with 1-(2-aminoethyl)piperidine (1.08 ml), thereby yielding 1.56 g(59%) of the aimed compound.

¹H-NMR (CDCl₃) δ (ppm) 7.04(2H,d,J=3.9 Hz), 5.55 (1H,t,J=5.4 Hz), 4.54(2H,t,J=5.4 Hz), 3.90(6H,s), 3.57–3.45 (2H,m), 3.63–3.40(6H,m), 1.74(3H,s), 1.67(3H,s), 1.60–1.48(3H,m).

Example 28

In a manner identical to Example 45, 4-prenyloxybenzoic acid(1.44 g) was subjected to a condensation reaction with 1-(2-aminoethyl)morphorine (1.00 ml), thereby yielding 1.77 g(80%) of the aimed compound.

m.p. 114.8°–115.5° C. ¹H-NMR (CDCl₃) δ (ppm) 7.73 (2H,d,J=8.8 Hz), 6.94(2H,d,J=8.8 Hz), 6.66(1H,bs), 5.49 (1H,t,J=5.4 Hz), 4.56(2H,d,J=6.8 Hz), 3.73(4H,t,J=4.4 Hz), 3.54(2H,q,J=5.8 Hz), 2.59(2H,t,J=5.9 Hz), 2.50 (4H,t,J=4.4 Hz), 1.81(3H,s), 1.76(3H,s).

Example 29

In a manner identical to Example 45, 3-geranyloxybenzoic acid(1.37 g) was subjected to a condensation reaction with 1-(2-aminoethyl)morphorine (0.70 ml), thereby yielding 1.73 g(90%) of the aimed compound.

m.p. 54.8°–57.2° C. ¹H-NMR (CDCl₃) δ (ppm) 7.41–7.25 (3H,m), 7.05(2H,dt,J=2.4 Hz,8.6 Hz), 6.74(1H,bs), 5.49(1H, t,J=6.3 Hz), 5.12–5.06(1H,m), 4.58(2H,d,J=6.3 Hz), 3.73 (4H,t,J=4.9 Hz), 3.55(2H,q,J=5.9 Hz), 2.60(2H,t,J=5.9 Hz), 2.55–2.41(4H,m), 2.16–2.04(4H,m), 1.75(3H,s), 1.68 (3H, s), 1.61(3H,s).

Example 30

In a manner identical to Example 45, 2-geranyloxybenzoic acid(1.37 g) was subjected to a condensation reaction with 1-(2-aminoethyl)morphorine (0.70 ml), thereby yielding 1.71 g(89%) of the aimed compound.

¹H-NMR (CDCl₃) δ (ppm) 8.33(1H,bs), 8.20(1H,dd,J= 1.5 Hz,7.8 Hz), 7.41(1H,dt,J=2.0 Hz,7.3 Hz), 7.06 (1H,t,J= 7.3 Hz), 6.96(1H,d,J=8.3 Hz), 5.49(1H,t,J=6.4 Hz), 5.09–5.01(1H,m), 4.73(2H,d,J=6.4 Hz), 3.72(4H,t,J=4.6 Hz), 3.58(2H,q,J=6.4 Hz), 2.57(2H,t,J=6.4 Hz), 2.53–2.44 (4H,m), 2.18–2.01(4H,m), 1.76(3H,s), 1.67(3H,s), 1.60(3H, s).

Example 31

In a manner identical to Example 45, 4-geranyloxybenzoic acid(1.37 g) was subjected to a condensation reaction with 1-(2-aminoethyl)morphorine (0.70 ml), thereby yielding 1.46 g(76%) of the aimed compound.

m.p. 85.2°–87.0° C. ¹H-NMR (CDCl₃) δ (ppm) 7.73(2H, d,J=8.6 Hz), 6.92(2H,d,J=8.6 Hz), 6.76(1H,bs), 5.57–5.43 (1H,m), 5.15–5.06(1H,m), 4.58(2H,d,J=6.3 Hz), 3.73(4H,t, J=4.7 Hz), 3.55(2H,q,J=5.9 Hz), 2.62 (2H,t,J=6.3 Hz), 2.59–2.48(4H,m), 222–2.04(4H,m), 1.74(3H,s), 1.68(3H,s), 1.60 (3H,s).

Example 32

In a manner identical to Example 45, 4-farnesyloxybenzoic acid(1.71 g) was subjected to a condensation reaction with 1-(2-aminoethyl)morphorine (0.70 ml), thereby yielding 2.18 g(96%) of the aimed compound.

m.p. 68.6°–71.2° C. ¹H-NMR (CDCl₃) δ (ppm) 7.73(2H, d,J=8.8 Hz), 6.94(2H,d,J=8.8 Hz), 6.66(1H,bs), 5.48(1H,t, J=5.4 Hz), 5.06–5.16(2H,m), 4.58(2H,d,J=5.4 Hz), 3.73(4H, t,J=4.4 Hz), 3.54(2H,q,J=5.4 Hz), 2.60 (2H,t,J=5.8 Hz), 2.45–2.55(4H,m), 2.17–1.92(6H,m), 1.75(3H,s), 1.68(3H,s), 1.60 (6H,s).

Example 33

In a manner identical to Example 45, 2-geranylthiobenzoic acid(2.03 g) was subjected to a condensation reaction with 1-(2-aminoethyl)morphorine (1.00 ml), thereby yielding 1.43 g(51%) of the aimed compound.

$^1$H-NMR (CDCl$_3$) δ (ppm) 7.67(1H,d,J=7.4 Hz), 7.41–7.39(1H,m), 7.35–7.23(2H,m), 5.27(1H,t,J=7.8 Hz), 5.04(1H,t,J=6.4 Hz), 4.73(2H,d,J=6.4 Hz), 3.70(4H,t,J=4.9 Hz), 3.60–3.54(4H,m), 2.60 (2H,t,J=6.4 Hz), 2.50(4H,t,J=5.4 Hz), 2.07–1.97(4H,m), 1.67(3H,s), 1.58(3H,s), 1.54 (3H, s).

Example 34

In a manner identical to Example 45, 4-geranyloxybenzoic acid(1.92 g) was subjected to a condensation reaction with 1-(2-aminoethyl)-2,6-dimethyl morphorine(1.00 g), thereby yielding 1.20 g(41%) of the aimed compound.

m.p. 74.6°–75.8° C. $^1$H-NMR (CDCl$_3$) δ (ppm) 7.72(2H, d,J=8.8 Hz), 6.90(2H,d,J=8.8 Hz), 6.72–6.92(1H,m), 5.38–5.54 (1H,m), 5.00–5.16(1H,m), 4.56(2H,d,J=6.4 Hz), 3.63–3.81(2H,m), 3.57(2H,q,J=5.9 Hz), 2.81(2H,d,J=10.7 Hz), 2.62(2H,t,J=5.9 Hz), 1.95–2.25(4H,m), 1.84(2H,t,J=10.7 Hz), 1.74 (3H,s), 1.68(3H,s), 1.60(3H,s), 1.17(6H,d,J=6.4 Hz).

Example 35

In a manner identical to Example 45, 3,4-diprenyloxybenzoic acid(1.45 g) was subjected to a condensation reaction with 1-(2-aminoethyl)morphorine(0.67 ml), thereby yielding 1.76 g(88%) of the aimed compound.

m.p. 119.0°–120.0° C. $^1$H-NMR (CDCl$_3$) δ (ppm) 7.43 (1H,d,J=2.0 Hz), 6.85(1H,d,J=8.3 Hz), 5.61–5.46(2H,m), 4.63(4H,d,J=6.8 Hz), 3.72(4H,t,J=4.3 Hz), 3.54(2H,q,J=5.9 Hz), 2.60(2H,t,J=5.9 Hz), 2.50(4H,d,J=4.4 Hz), 1.77(6H,s), 1.74(3H,s), 1.73(3H,s).

Example 36

In a manner identical to Example 45, 3,4-digeranyloxybenzoic acid(2.13 g) was subjected to a condensation reaction with 1-(2-aminoethyl)morphorine(0.70 ml), thereby yielding 2.29 g(85%) of the aimed compound.

m.p. 113.5°–114.0° C. $^1$H-NMR (CDCl$_3$) δ (ppm) 7.43 (1H,d,J=2.0 Hz), 7.28–7.23(1H,m), 6.87(1H,d,J=8.3 Hz), 5.56–5.45 (2H,m), 5.13–5.02(2H,m), 4.65(4H,d,J=6.4 Hz), 3.78–3.65(4H,m), 3.58–3.46(2H,m), 2.63–2.54(2H,m), 2.53–2.44(4H,m), 2.16–2.00(8H,m), 1.74(3H,s), 1.72(3H,s), 1.67 (6H,s), 1.60(6H,s).

Example 37

In a manner identical to Example 45, 2,4-digeranyloxybenzoic acid(2.13 g) was subjected to a condensation reaction with 1-(2-aminoethyl)morphorine(0.70 ml), thereby yielding 2.21 g(82%) of the aimed compound.

$^1$H-NMR (CDCl$_3$) δ (ppm) 8.24–8.12(2H,m), 6.59(1H,d, J=8.8 Hz), 6.50(1H,s), 5.54–5.43(2H,m), 5.09–5.07(2H,m), 4.64(2H,d,J=6.4 Hz), 4.54(2H,d,J=6.8 Hz), 3.24–3.18(4H, m), 3.56(2H,q,J=6.4 Hz), 2.56(2H,t,J=6.4 Hz), 2.15–2.05 (8H,m), 1.74(6H,s), 1.68–1.67(6H,m).

Example 38

In a manner identical to Example 45, 3,5-digeranyloxybenzoic acid(2.13 g) was subjected to a condensation reaction with 1-(2-aminoethyl)morphorine(0.70 ml), thereby yielding 1.67 g(62%) of the aimed compound.

$^1$H-NMR (CDCl$_3$) δ (ppm) 6.92(2H,d,J=2.0 Hz), 6.61 (1H,s), 5.49(2H,t,J=6.4 Hz), 5.12–5.04(2H,m), 4.54 (4H,d, J=6.8 Hz), 3.72(4H,t,J=4.9 Hz), 3.58(2H,q,J=5.9 Hz), 2.58 (2H,t,J=6.3 Hz), 2.53–2.48(4H,m), 2.17–2.04(8H,m), 1.73 (6H,s), 1.68(6H,s), 1.60(6H,s).

Example 39

In a manner identical to Example 45, 3,4,5-triprenyloxybenzoic acid(14.98 g) was subjected to a condensation reaction with 1-(2-aminoethyl)morphorine(5.73 g), thereby yielding 13.54 g(70%) of the aimed compound.

m.p. 72.0°–75.0° C. $^1$H-NMR (CDCl$_3$) δ (ppm) 7.00(2H, s), 6.60(1H,s), 5.57–5.41(3H,m), 4.62–4.45(6H,m), 3.75–3.63 (4H,m), 3.56–3.45(2H,m), 2.62–2.53(2H,m), 2.52–2.40(4H,m), 1.78–1.55(18H,m).

Example 40

In a manner identical to Example 45, 2-geranyloxy-5-methoxybenzoic acid (1.52 g) was subjected to a condensation reaction with 1-(2-aminoethyl) morphorine(0.70 ml), thereby yielding 1.93 g(93%) of the aimed compound.

$^1$H-NMR (CDCl$_3$) δ (ppm) 8.45(1H,bs), 7.76(1H,d,J=3.0 Hz), 7.06–6.82(2H,m), 5.77–5.50(1H,m), 5.10–494(1H,m), 4.67(2H,d,J=6.8 Hz), 3.81(3H,s), 3.73–3.48(6H,m), 2.61–2.39 (6H,m), 2.14–1.92(4H,m), 1.73(3H,s), 1.67(3H, s), 1.60(3H,s).

Example 41

In a manner identical to Example 45, 3,5-dimethoxy-4-prenyloxybenzoic acid (0.80 g) was subjected to a condensation reaction with 1-(2-aminoethyl) morphorine(0.42 g), thereby yielding 0.96 g(85%) of the aimed compound.

m.p. 116.0°–118.0° C. $^1$H-NMR (CDCl$_3$) δ (ppm) 7.00 (2H,s), 6.66(1H,s), 5.57–5.53(1H,m), 4.54(2H,d,J=7.3 Hz), 3.89(6H,s), 3.72(4H,t,J=4.7 Hz), 3.57–3.52(2H,m), 2.61 (2H,t,J=6.4 Hz), 2.51(4H,d,J=4.9 Hz), 1.74 (3H,s), 1.68(3H, s).

Example 42

In a manner identical to Example 45, 3,5-dimethoxy-4-geranyloxybenzoic acid (0.80 g) was subjected to a condensation reaction with 1-(2-aminoethyl) morphorine(0.31 g), thereby yielding 0.74 g(69%) of the aimed compound.

m.p. 86.0°–89.0° C. $^1$H-NMR (CDCl$_3$) δ (ppm) 6.99(2H, s), 6.68(1H,s), 5.59–5.50(1H,m), 5.12–5.03(1H,m), 4.57 (2H,d,J=7.3 Hz), 3.89(6H,s), 3.76–3.67(4H,m), 3.60–3.55 (2H,m), 2.65–2.58(2H,m), 2.57–2.47(4H,m), 2.13–1.98(4H, m), 1.66(3H,s), 1.65(3H,s), 1.58(3H,s).

Example 43

In a manner identical to Example 45, 3,5-dimethoxy-4-neryloxybenzoic acid (1.10 g) was subjected to a condensation reaction with 1-(2-aminoethyl) morphorine(0.43 g), thereby yielding 1.46 g(99%) of the aimed compound.

$^1$H-NMR (CDCl$_3$) δ (ppm) 7.00(2H,s), 6.68–6.78(1H,bs), 5.56(1H,t,J=5.4 Hz), 5.08(1H,t,J=5.4 Hz), 4.54 (2H,d,J=6.8 Hz), 3.89(6H,s), 3.74–3.71(4H,m), 3.57–3.53(2H,m), 2.62 (2H,t,J=6.4 Hz), 2.53(4H,t,J=4.4 Hz), 2.14–2.01(4H,m), 1.75(3H,s), 1.67(3H,s), 1.58(3H,s).

Example 44

In a manner identical to Example 45, 4,5-dimethoxy-3-geranyloxybenzoic acid (1.34 g) was subjected to a condensation reaction with 1-(2-aminoethyl) morphorine(0.58 ml), thereby yielding 0.80 g(45%) of the aimed compound.

¹H-NMR (CDCl₃) δ (ppm) 7.04(2H,s), 6.94–6.86(1H,bs), 5.51(1H,t,J=5.4 Hz), 5.08(1H,t,J=5.4 Hz), 4.63 (2H,d,J=6.4 Hz), 3.89(6H,s), 3.73–3.69(4H,m), 3.57–3.52(2H,m), 2.61 (2H,t,J=5.8 Hz), 2.56–2.48(4H,m), 2.17–2.04(4H,m), 1.74 (3H,s), 1.66(3H,s), 1.60(3H,s).

Example 45

To a solution of 4-geranyloxybenzoic acid(1.92 g) in chloroform(30 ml) were added triethylamine(2.09 ml) and diphenylphosphinic chloride(1.43 ml) while being cooled with ice. After being stirred for 30 minutes, the mixture, with 4-(2-aminoethyl)-1-ethylpiperazine(1.48 g) added thereto, was stirred for 2 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=15:1). The resulting solid was recrystallized from hexane, thereby yielding 0.84 g(41%) of the aimed compound.

m.p. 65.2°–66.9° C. ¹H-NMR (CDCl₃) δ (ppm) 7.73(2H, d, J=8.8 Hz), 6.93(2H, d, J=8.8 Hz), 6.75(1H, s), 5.48(1H, t, J=6.4 Hz), 5.09(1H, t, J=6.8 Hz), 4.58(2H, d, J=6.4 Hz), 3.27(2H, q, J=5.8 Hz), 2.62–2.20(12H, m), 2.19–2.04(4H, m), 1.74(3H, s), 1.67(3H, s), 1.60(3H, s), 1.10(3H, t, J=6.3 Hz).

Example 46

In a manner identical to Example 45, 4-geranyloxybenzoic acid(1.10 g) was subjected to a condensation reaction with 4-(2-aminoethyl)-1-isobutylpiperazine (1.19 g), thereby yielding 0.75 g(42%) of the aimed compound.

m.p. 74.0°–75.0° C. ¹H-NMR (CDCl₃) δ (ppm) 7.73(2H, d, J=8.8 Hz), 6.94(2H, d, J=8.8 Hz), 6.78(1H, s), 5.48(1H, t, J=6.8 Hz), 5.09(1H, t, J=6.4 Hz), 4.58(2H, d, J=6.4 Hz), 3.52(2H, q, J=5.4 Hz), 2.59(2H, t, J=5.8 Hz), 2.53(4H, s), 2.43(4H, s), 2.19–2.04(6H, m), 1.77 (1H, n, J=6.8 Hz), 1.74 (3H, s),1.68(3H,s), 1.60(3H, s), 0.89(6H, d, J=6.8 Hz).

Example 47

In a manner identical to Example 45, 4-geranyloxybenzoic acid(1.10 g) was subjected to a condensation reaction with 4-(2-aminoethyl)-1-isoamylpiperazine (1.19 g), thereby yielding 0.73 g(40%) of the aimed compound.

m.p. 75.0°–76.8° C. ¹H-NMR (CDCl₃) δ (ppm) 7.73(2H, d, J=8.8 Hz), 6.94(2H, d, J=8.8 Hz), 6.73(1H, s), 5.48(1H, t, J=6.1 Hz), 5.14–5.04(1H, m), 4.58(2H, d, J=6.8 Hz), 3.53(2H, q, J=5.4 Hz), 2.61–2.33 (10H, m), 2.19–2.04(4H, m), 1.74 (3H, s), 1.68(3H,s), 1.65–1.55(6H,m),1.42–1.36 (2H, m), 0.90(2H, d, J=6.4 Hz).

Example 48

In a manner identical to Example 45, 4-geranyloxybenzoic acid(1.37 g) was subjected to a condensation reaction with 4-(2-aminoethyl)-1-neopentylpiperazine (1.49 g), thereby yielding 0.64 g(28%) of the aimed compound.

m.p. 72.0°–73.4° C. ¹H-NMR (CDCl₃) δ (ppm) 7.73(2H, d, J=8.8 Hz), 6.94(2H, d, J=8.8 Hz), 6.76(1H, s), 5.48(1H, t, J=6.4 Hz), 5.09(1H, t, J=6.4 Hz), 4.58(2H, d, J=6.8 Hz), 3.52(2H, q, J=5.9 Hz), 2.58–2.48(10H, m), 2.17–2.06(6H, m), 1.74(3H, s), 1.68(3H,s), 1.61(3H,s), 0.86(9H, s).

Example 49

In a manner identical to Example 45, 4-geranyloxybenzoic acid(1.65 g) was subjected to a condensation reaction with 4-(2-aminoethyl)-1-(2-ethylbutyl) piperazine(1.91 g), thereby yielding 1.01 g(36%) of the aimed compound.

m.p. 59.3°–60.1° C. ¹H-NMR (CDCl₃) δ (ppm) 7.73(2H, d, J=8.8 Hz), 6.94(2H, d, J=8.8 Hz), 6.74(1H, s), 5.48(1H, t, J=6.1 Hz), 5.09(1H, t, J=6.8 Hz), 4.58(2H, d, J=6.4 Hz), 3.52(2H, q, J=5.4 Hz), 2.58(2H, t, J=5.8 Hz), 2.51(2H, s), 2.43(4H, s), 2.16–2.07(6H, m), 1.74(3H, s), 1.68(3H,s), 1.61 (3H, s), 1.45–1.24(5H, m), 0.86(6H, t, J=7.5 Hz).

Example 50

In a manner identical to Example 45, 4-geranyloxybenzoic acid(1.88 g) was subjected to a condensation reaction with 4-(2-aminoethyl)-1-n-butylpiperazine (3.04 g), thereby yielding 1.29 g(46%) of the aimed compound.

m.p. 64.3°–65.9° C. ¹H-NMR (CDCl₃) δ (ppm) 7.73(2H, d, J=8.8 Hz), 6.94(2H, d, J=8.8 Hz), 6.70(1H, s), 5.48(1H, t, J=5.9 Hz), 5.09(1H, t, J=6.8 Hz), 4.58(2H, d, J=6.8 Hz), 3.52(2H, q, J=5.4 Hz), 2.61–2.40(8H, m), 2.34(2H, t, J=7.8 Hz), 2.28–2.07(4H, m), 1.74 (3H, s),1.68(3H,s), 1.61 (3H, s), 1.54–1.44(2H, m), 1.37–1.27(2H, m), 0.92(3H, t, J=7.3 Hz).

Example 51

In a manner identical to Example 45, 4-geranyloxybenzoic acid(1.92 g) was subjected to a condensation reaction with 4-(2-aminoethyl)-1-(2-ethylhexyl) piperazine(2.03 g), thereby yielding 1.46 g(42%) of the aimed compound.

m.p. 48.0°–49.0° C. ¹H-NMR (CDCl₃) δ (ppm) 7.73(2H, d, J=8.8 Hz), 6.94(2H, d, J=8.8 Hz), 6.74(1H, s), 5.48(1H, t, J=5.9 Hz), 5.09(1H, t, J=6.8 Hz), 4.58(2H, d, J=6.8 Hz), 3.51(2H, q, J=5.9 Hz), 2.58(2H, t, J=6.1 Hz), 2.50–2.42(8H, m), 2.19–2.04(4H, m), 1.78 (3H,s), 1.68(3H,s), 1.61(3H, s), 1.46–1.26(9H, m), 0.91–0.83(6H, m).

Example 52

In a manner identical to Example 45, 4-geranyloxybenzoic acid(1.37 g) was subjected to a condensation reaction with 4-(2-aminoethyl)-1-phenylpiperazine (1.54 g), thereby yielding 1.57 g(68%) of the aimed compound.

m.p. 154.0°–156.0° C. ¹H-NMR (CDCl₃) δ (ppm) 7.73 (2H, d, J=8.8 Hz), 7.30–7.22(2H, m), 6.95–6.92(4H, m), 6.87(1H, t, J=6.8 Hz), 6.73(1H, s), 5.47(1H, t, J=6.8 Hz), 5.08(1H, t, J=6.8 Hz), 4.58(2H, d, J=6.4 Hz), 3.58(1H, q, J=5.4 Hz), 2.67(6H, t, J=5.8 Hz), 2.19–2.04(4H, m), 1.74 (3H, s), 1.67(3H,s), 1.60(3H, s).

Example 53

In a manner identical to Example 45, 4-geranyloxybenzoic acid(1.92 g) was subjected to a condensation reaction with 4-(2-aminoethyl)-1-(4-methoxyphenyl) piperazine(3.01 g), thereby yielding 2.85 g(70%) of the aimed compound.

m.p. 159.0°–160.0° C. ¹H-NMR (CDCl₃) δ (ppm) 7.73 (2H, d, J=8.8 Hz), 6.90–6.83(6H, m), 6.73(1H, s), 5.48(1H, t, J=6.8 Hz), 5.09(1H, t, J=6.4 Hz), 4.58(2H, d, J=6.4 Hz), 3.77(3H,s), 3.57(2H, q, J=5.8 Hz), 3.12 (4H,t, J=4.9 Hz), 2.68(6H, t, J=5.4 Hz), 2.19–2.04(4H, m), 1.74 (3H, s), 1.67(3H,s), 1.60 (3H, s).

Example 54

In a manner identical to Example 45, 4-geranyloxybenzoic acid(2.80 g) was subjected to a condensation reaction with 4-(2-aminoethyl)-1-(isopropylcarbamoyl methyl)piperazine (1.98 g), thereby yielding 2.21 g(65%) of the aimed compound as pale yellow oil.

1H-NMR (CDCl$_3$) δ (ppm) 7.72(2H, d, J=8.8 Hz), 6.94 (2H, d, J=8.8 Hz), 6.91(1H, s), 6.69(1H, s), 5.48 (1H, t, J=6.4 Hz), 5.09(1H, t, J=6.8 Hz), 4.58(2H, d, J=6.8 Hz), 4.10(1H, d, J=5.4 Hz), 3.54(2H, q, J=5.8 Hz), 2.98(2H, s), 2.61(4H, t, J=5.8 Hz), 2.56(6H, s), 2.19–2.04(4H, m), 1.74 (3H, s), 1.67(3H,s), 1.60(3H, s), 1.17(6H, d, J=6.8 Hz).

Example 55

In a manner identical to Example 45, 4-geranyloxybenzoic acid(1.65 g) was subjected to a condensation reaction with 4-(2-aminoethyl)-1-(pyroridinocarbonyl methyl)piperazine (2.86 g), thereby yielding 1.22 g(41%) of the aimed compound as pale yellow oil.

$^1$H-NMR (CDCl$_3$) δ (ppm) 7.73(2H, d, J=8.8 Hz), 6.92 (2H, d, J=8.8 Hz), 6.84(1H, s), 5.48(1H, t, J=5.4 Hz), 5.09(1H, t, J=5.8 Hz), 4.58(2H, d, J=6.4 Hz), 3.54(2H, q, J=5.4 Hz), 3.52–3.40(4H, m), 3.14(2H, s), 2.73–2.39(10H, m), 2.19–2.04(4H, m), 1.95 (2H, q, J=6.8 Hz), 1.85(2H, q, J=6.8 Hz), 1.75(3H, s), 1.68(3H,s), 1.61(3H, s).

Example 56

In a manner identical to Example 45, 4-geranyloxybenzoic acid(1.65 g) was subjected to a condensation reaction with 4-(2-aminoethyl)-1-benzylpiperazine (1.97 g), thereby yielding 2.14 g(75%) of the aimed compound.

m.p. 80.0°–81.0° C. $^1$H-NMR (CDCl$_3$) δ (ppm) 7.72(2H, d, J=8.8 Hz), 7.32–7.23(5H, m), 6.94(2H, d, J=8.8 Hz), 6.72(1H, s), 5.48(1H, t, J=6.4 Hz), 5.09(1H, t, J=6.8 Hz), 4.59(2H, d, J=6.4 Hz), 3.52(2H, s), 3.51 (2H, q, J=5.8 Hz), 2.59(6H, t, J=5.8 Hz), 2.52(4H, s), 2.19–2.04(4H, m), 1.75 (3H, s), 1.68(3H,s), 1.61(3H, s).

Example 57

In a manner identical to Example 45, 4-geranyloxybenzoic acid(1.10 g) was subjected to a condensation reaction with 4-(2-aminoethyl)-1-(4-fluorobenzyl) piperazine (1.63 g), thereby yielding 1.12 g(57%) of the aimed compound.

m.p. 95.0°–96.0° C. $^1$H-NMR (CDCl$_3$) δ (ppm) 7.72(2H, d, J=8.8 Hz), 7.32–7.26(2H, m), 7.02–6.96(2H, m), 6.94(2H, d, J=8.8 Hz), 6.70(1H, s), 5.48(1H, t, J=6.4 Hz), 5.09(1H, t, J=6.4 Hz), 4.59(2H, d, J=6.4 Hz), 3.52(2H, q, J=5.8 Hz), 3.48(2H, s), 2.59(2H, t, J=5.8 Hz), 2.58–2.30(8H, m), 2.19–2.04(4H, m), 1.75 (3H, s), 1.68(3H,s), 1.61(3H, s).

Example 58

In a manner identical to Example 45, 4-geranyloxybenzoic acid(1.10 g) was subjected to a condensation reaction with 4-(2-aminoethyl)-1-(3,4-methylenedioxybenzyl)piperazine(1.36 g), thereby yielding 0.96 g(46%) of the aimed compound.

m.p. 90.8°–92.5° C. $^1$H-NMR (CDCl$_3$) δ (ppm) 7.73(2H, d, J=8.8 Hz), 6.94(2H, d, J=8.8 Hz), 6.85(1H, s), 6.74(2H, d, J=1.0 Hz), 5.94(2H, s), 5.48(1H, t, J=6.4 Hz), 5.09(1H, t, J=6.8 Hz), 4.58(2H, d, J=6.4 Hz), 3.52(2H, q, J=5.4 Hz), 3.43(2H, s), 2.64–2.34(10H, m), 2.19–2.04(4H, m), 1.75 (3H, s), 1.68(3H,s), 1.61(3H, s).

Example 59

In a manner identical to Example 45, 4-geranyloxybenzoic acid(1.65 g) was subjected to a condensation reaction with 4-(2-aminoethyl)-1-(2-benzothiazolyl) piperazine(1.88 g), thereby yielding 2.30 g(74%) of the aimed compound.

m.p. 136.0°–138.0° C. $^1$H-NMR (CDCl$_3$) δ (ppm) 7.33 (2H, d, J=8.8 Hz), 7.61(1H, d, J=6.4 Hz), 7.56(1H, d, J=7.8 Hz), 7.30(1H, t, J=6.8 Hz), 7.09(1H, t, J=6.8 Hz), 6.94(2H, d, J=8.8 Hz), 6.33(1H, s), 5.47(1H, t, J=6.4 Hz), 5.08(1H, t, J=6.8 Hz), 4.58(2H, d, J=6.4 Hz), 3.68(4H, t, J=4.9 Hz), 3.59(2H, q, J=5.4 Hz), 2.82–2.04(6H,m), 2.19–2.04(4H, m), 1.74(3H, s), 1.67(3H, s), 1.60(3H, s).

Example 60

In a manner identical to Example 45, 4-geranyloxybenzoic acid(1.10 g) was subjected to a condensation reaction with 4-(2-aminoethyl)-1-(2-thiazolyl) piperazine (1.34 g), thereby yielding 0.55 g(29%) of the aimed compound.

m.p. 121.3°–122.4° C. $^1$H-NMR (CDCl$_3$) δ (ppm) 7.73 (2H, d, J=8.3 Hz), 7.21(1H, d, J=3.9), 6.93(2H, d, J=8.8 Hz), 6.65(1H, s), 6.59(1H, d, J=3.4 Hz), 5.47(1H, t, J=6.4 Hz), 5.09(1H, t, J=6.8 Hz), 4.58(2H, d, J=6.4 Hz), 3.58(2H, q, J=5.8 Hz), 3.53(4H, t, J=4.9 Hz), 2.71–2.60(6H, m), 2.19–2.04 (4H, m), 1.74 (3H, s), 1.67(3H,s), 1.60(3H, s).

Example 61

In a manner identical to Example 45, 4-geranyloxybenzoic acid(1.10 g) was subjected to a condensation reaction with 4-(2-aminoethyl)-1-(2-pyrimidinyl) piperazine(2.00 g), thereby yielding 0.89 g(48%) of the aimed compound.

m.p. 106.0°–107.2° C. $^1$H-NMR (CDCl$_3$) δ (ppm) 8.31 (2H, d, J=4.4 Hz), 7.74(2H, d, J=8.8 Hz), 6.92(2H, d, J=8.8 Hz), 6.50(1H, t, J=4.9 Hz), 5.47(1H, t, J=6.4 Hz), 5.09(1H, t, J=6.8 Hz), 4.57(2H, q, J=6.8 Hz), 3.87 (4H, s), 3.60(2H, q, J=5.8 Hz), 2.68(2H, t, J=5.8 Hz), 2.67–2.54(4H, m), 2.19–2.04 (4H, m), 1.74 (3H, s), 1.67(3H,s), 1.60(3H, s).

Example 62

4-(4-Fluorobenzyloxy)-3-isobutylbenzoic acid(2.00 g) was dissolved in methylene chloride(25 ml) and triethylamine(1.73 g), and then diphenylphosphinic chloride (1.75 g) was added thereto while being cooled with ice. After being stirred for 40 minutes, the mixture, with 4-(2-aminoethyl)-1-isobutylpiperazine(1.85 g) added thereto, was stirred overnight at room temperature. The reaction mixture was washed with water, dried over magnesium sulfate, and then filtrated. The filtrate was concentrated under a vacuum and the residue was purified by silica gel column chromatography (chloroform:methanol=20:1). The resulting solid was recrystallized from n-hexane, thereby yielding 0.95 g of colorless crystals. The crystals was dissolved in chloroform and then 1N hydrochloric acid ether solution was added thereto. The reaction mixture was stirred at room temperature for 10 minutes. The depositing solid was collected by filtration and recrystallized from ethanol/ ethyl acetate mixed solution, thereby yielding 1.03 g(29%) of the aimed compound as white crystals.

m.p. 173.0°–174.0° C. $^1$H-N (CDCl$_3$) δ (ppm) 13.03(1H, s), 8.13(1H, s), 7.87(1H, d, J=8.8 Hz), 7.83(1H, s), 7.38(2H, t, J=5.8 Hz), 7.08(2H, t, J=8.8 Hz), 6.91(1H, d, J=8.8 Hz), 5.07(2H, s), 4.50–4.30(2H, bs), 4.04–3.96(2H, m), 3.90(2H, s), 3.64(4H, t, J=14.7 Hz), 3.40(2H, s), 2.94(2H, d, J=6.4 Hz), 2.55(2H, d, J=4.9 Hz), 2.01–1.91(1H, m), 1.88–1.71 (1H, m), 1.15(6H, d, J=6.8 Hz), 0.89(6H, d, J=6.8 Hz).

What is claimed is:

1. An alkylenediamine derivative or a salt thereof expressed by the following formula 1:

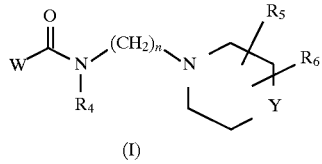

wherein W represents a group expressed by the following formula 2 or formula 3;

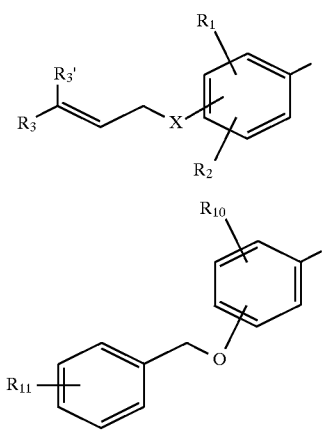

wherein each of $R_1$ and $R_2$ represents hydrogen atom, a lower alkoxy group, an alkenyloxy group, or a halogen atom;

each of $R_3$ and $R_3'$ represents methyl group, prenyl group, or geranyl group and when one of $R_3$ and $R_3'$ is prenyl group or geranyl group, another is methyl group;

X represents oxygen atom or sulfur atom;

$R_{10}$ represents a lower alkyl group; and $R_{11}$ represents a halogen atom; and wherein each of $R_4$, $R_5$, and $R_6$ represents hydrogen atom or a lower alkyl group;

Y represents a group expressed by —$CH_2$—, —O—, or —$N(R_7)$—, while $R_7$ represents a lower alkyl group, an aryl group, a carbamoyl lower alkyl group, an aralkyl group, or a heterocyclic group having 5 to 9 members; and n represents an integer of 1 to 6.

2. An alkylenediamine derivative or a salt thereof according to claim 1, which expressed by the following formula 4.

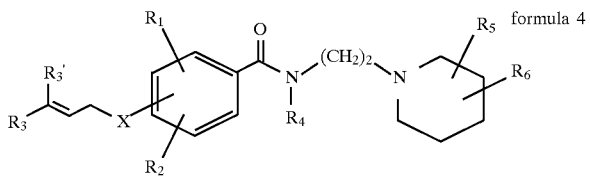

wherein $R_1$, $R_2$, $R_3$, $R_3'$, $R_4$, $R_5$, $R_6$, and X are same as those in the above-mentioned formula 1.

3. An alkylenediamine derivative or a salt thereof according to claim 2, wherein X is oxygen atom, while $R_4$, $R_5$, and $R_6$ are hydrogen atoms.

4. An alkylenediamine derivative or a salt thereof according to claim 3, wherein $R_1$ and $R_2$ are hydrogen atoms.

5. An alkylenediamine derivative or a salt thereof according to claim 3, wherein $R_1$ and/or $R_2$ is an alkenyloxy group expressed by the following formula 5;

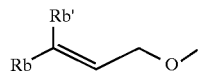

wherein each of $R_b$ and $R_b'$ represents methyl group, prenyl group, or geranyl group and when one of $R_b$ and $R_b'$ is prenyl group or geranyl group, another is methyl group.

6. An alkylenediamine derivative or a salt thereof according to claim 3, wherein $R_1$ and/or $R_2$ is a lower alkoxy group.

7. An alkylenediamine derivative or a salt thereof according to claim 1, which expressed by the following formula 6.

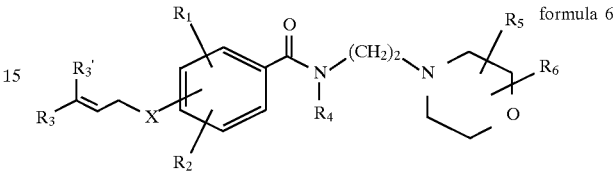

wherein $R_1$, $R_2$, $R_3$, $R_3'$, $R_4$, $R_5$, $R_6$, and X are same as those in the above-mentioned formula 1.

8. An alkylenediamine derivative or a salt thereof according to claim 7, wherein X is oxygen atom, while $R_4$, $R_5$, and $R_6$ are hydrogen atoms.

9. An alkylenediamine derivative or a salt thereof according to claim 8, wherein $R_1$ and $R_2$ are hydrogen atoms.

10. An alkylenediamine derivative or a salt thereof according to claim 8, wherein $R_1$ and/or $R_2$ is an alkenyloxy group expressed by above-mentioned formula 5.

11. An alkylenediamine derivative or a salt thereof according to claim 8, wherein $R_1$ and/or $R_2$ is a lower alkoxy group.

12. An alkylenediamine derivative or a salt thereof according to claim 1, which expressed by the following formula 7;

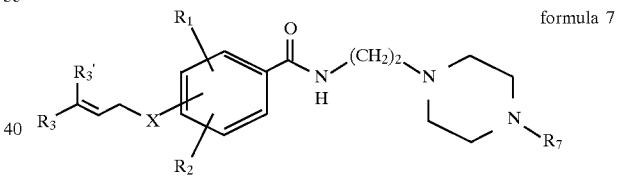

wherein $R_1$, $R_2$, $R_3$, $R_3'$, $R_7$, and X are same as those in the above-mentioned formula 1.

13. An alkylenediamine derivative or a salt thereof according to claim 12, wherein X is oxygen atom, while $R_1$ and $R_2$ are hydrogen atoms.

14. An alkylenediamine derivative or a salt thereof according to claim 1, which expressed by the following formula 8;

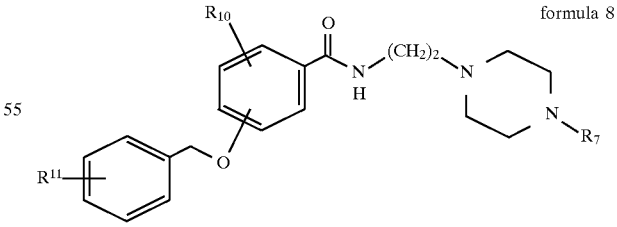

wherein $R_7$ is a lower alkyl group; and $R_{10}$ and $R_{11}$ are same as those in the above-mentioned formula 3.

15. An alkylenediamine derivative or a salt thereof according to claim 14, wherein $R_7$ and $R_{10}$ are isobutyl groups.

16. An alkylenediamine derivative or a salt thereof according to claim 14 or 15, wherein $R_{11}$ is fluorine atom bonded to para-position.

17. An anti-ulcer drug comprising, as an effective ingredient, an alkylenediamine derivative or a pharmacologically acceptable salt thereof according to claim 1, together with a pharmaceutically acceptable carrier and/or adjuvant.

18. An antibacterial drug against *Helicobacter pyroli* comprising, as an effective ingredient, an alkylenediamine derivative or a pharmacologically acceptable salt thereof according to claim 1, together with a pharmaceutically acceptable carrier and/or adjuvant.

19. A method for the treatment of peptic ulcers in man or mammals, which comprises administering an effective amount of an alkylenediamine derivative or a pharmacologically acceptable salt thereof according to claim 1 to a host.

20. A method according to claim 19, wherein said peptic ulcers are gastric ulcers in man.

21. A method for the inhibition of acid secretion in stomach of man or mammals, which comprises administering an effective amount of an alkylenediamine derivative or a pharmacologically acceptable salt thereof according to claim 1 to a host.

22. A method for the inhibition of growth of *Helicobacter pyroli* in stomach of man or mammals, which comprises administering an effective amount of an alkylenediamine derivative or a pharmacologically acceptable salt thereof according to claim 1 to a host.

23. A method for the prevention of peptic ulcers in man or mammals, which comprises administering an effective amount of an alkylenediamine derivative or a pharmacologically acceptable salt thereof according to claim 1 to a host.

24. A method according to claim 23, wherein said peptic ulcers are gastric ulcers in man.

25. An alkylenediamine derivative or a salt thereof according to claim 14, wherein $R_{10}$ and —O—($CH_2$)—$C_6H_4$—$R_{11}$ are at positions 3 and 4 of the benzene ring.

26. An alkylenediamine derivative or a salt thereof having the following formula:

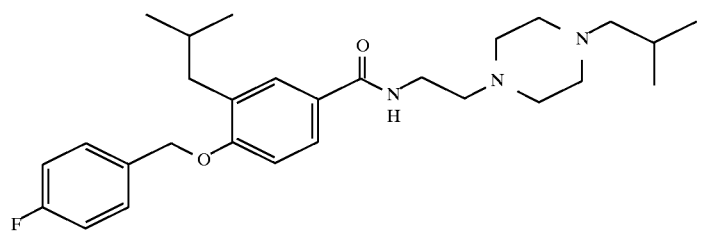

* * * * *